US012805963B2

(12) United States Patent
Weinstein

(10) Patent No.: US 12,805,963 B2
(45) Date of Patent: Nov. 24, 2026

(54) TISSUE EXPANDER DEVICE CREATING A SCARLESS NEO-UMBILICUS IN THE SURGICAL FIELD

(71) Applicant: Andrew L. Weinstein, New York, NY (US)

(72) Inventor: Andrew L. Weinstein, New York, NY (US)

( * ) Notice: Subject to any disclaimer, the term of this patent is extended or adjusted under 35 U.S.C. 154(b) by 769 days.

(21) Appl. No.: 18/130,922

(22) Filed: Apr. 5, 2023

(65) Prior Publication Data

US 2023/0338106 A1 Oct. 26, 2023

Related U.S. Application Data

(60) Provisional application No. 63/327,819, filed on Apr. 6, 2022.

(51) Int. Cl.
*A61B 90/00* (2016.01)

(52) U.S. Cl.
CPC .................................... *A61B 90/02* (2016.02)

(58) Field of Classification Search
CPC .......... A61B 90/02; A61B 2017/00796; A61B 2017/00557; A61B 2017/00792; A61B 2017/22051; A61F 2/12; A61F 2250/0003; A61F 2250/0067; A61M 29/00; A61M 29/02; A61M 2029/025; A61J 13/00
See application file for complete search history.

(56) References Cited

U.S. PATENT DOCUMENTS 4,984,585 A * 1/1991 Austad .................... A61B 90/02 623/8
5,655,545 A * 8/1997 Johnson ................. A61B 90/02 128/898
10,792,121 B2 * 10/2020 Jones ......................... A61F 2/12

FOREIGN PATENT DOCUMENTS

WO WO-2014175365 A1 * 10/2014 ............. A61B 90/02

OTHER PUBLICATIONS

Kadri, O.M. et al., Abdominoplasty Revision Using Tissue Expansion, Aesthetic Plast. Surg., June, pp. 538-540 (Year: 2013).*
Kadri (Year: 2013).*
Boudreault et al., "Getting the Best Results in Abdominoplasty: Current Advanced Concepts", Plast Reconstr Surg., 2019, 143(3), p. 628e-636e, Doi: 10.1097/PRS.0000000000005378.
Da Silva Jr et al., "Improvement on the Neo-umbilicoplasty Technique and Review of the Literature", Aesthet Plast Surg., 2017, 41(3), pp. 600-607, DOI: 10.1007/s00266-017-0847-6.

(Continued)

*Primary Examiner* — Sarah W Aleman
*Assistant Examiner* — Paris Marie Blass
(74) *Attorney, Agent, or Firm* — Gearhart Law LLC

(57) ABSTRACT

A novel tissue expander device is described herein. The device creates a scarless, natural-appearing neo-umbilicus in the surgical field either when one does not exist due to congenital or acquired causes, or when performing a full abdominoplasty necessitating umbilical repositioning. Specifically, the device can be anchored to the undersurface of the abdominal skin at the most aesthetic location for an umbilicus, and injected with saline to fill an expander balloon in the postoperative setting over the course of days to weeks to grow a skin tube. The device is removed during a second procedure to allow the skin tube to be inverted and attached to the abdominal wall fascia as a neo-umbilicus.

10 Claims, 30 Drawing Sheets

(56) References Cited

OTHER PUBLICATIONS

Grazer, "Abdominoplasty", Plast. Reconstr. Surg., Jun. 1973, 51(6), pp. 617-623.
International Society of Aesthetic Plastic Surgery, "International study on aesthetic/cosmetic procedures performed in 2013", Hanover: International Society of Aesthetic Plastic Surgery; 2014, 16 pages.
International Society of Aesthetic Plastic Surgery, "International study on aesthetic/cosmetic procedures performed in 2019", Hanover: International Society of Aesthetic Plastic Surgery; 2019, 55 pages.
Joseph et al., "Creating the Perfect Umbilicus: A Systematic Review of Recent Literature", Aesthet Plast Surg., 2016, 40(3), pp. 372-379, DOI: 10.1007/s00266-016-0633-x.
Kadri et al., "Abdominoplasty Revision Using Tissue Expansion", Aesthetic Plast Surg., Jun. 2013, 37(3), pp. 538-540, DOI: 10.1007/s00266-013-0104-6.
Kelly, "Excision of the fat of the abdominal wall lipectomy", Surg Gynecol Obstet., 1910, 10.
Lee et al., "Computer-Aided Analysis of the 'Beautiful' Umbilicus", Aesthet Surg J., 2014, 34(5), pp. 748-756, Doi: 10.1177/1090820X14533565.
Malic et al., "Patient Satisfaction with Two Different Methods of Umbilicoplasty", Plast Reconstr Surg., 2007, 119(1), pp. 357-361, DOI: 10.1097/01.prs.0000244907.06440.f8.
Matarasso et al., "Abdominoplasty and abdominal contour surgery: a national plastic surgery survey", Plast Reconstr Surg., 2006, 117, pp. 1797-1808.
Mejia, "Colombian Clover Umbilicoplasty: Achieving a Natural Looking Belly Button", Aesthet. Surg. J., 2019, 40(3), pp. 342-347, DOI: 10.1093/asj/sjz311.
Pitanguy, "Abdominal lipectomy: an approach to it through an analysis of 300 consecutive cases", Plast Reconstr Surg., 1967, 40, pp. 384-391.
Reho et al., 'Scarless reverse umbilicoplasty': A new technique of umbilical transposition in abdominoplasty, J Plastic Reconstr Aesthetic Surg., 2019, 72(4), pp. 656-661, DOI: 10.1016/j.bjps.2019.01.024.
Rohrich, et al., "Is the Umbilicus Truly Midline? Clinical and Medicolegal Implications", Plast. Reconstr. Surg., 2003, 112(1), pp. 259-263, Doi: 10.1097/01.PRS.0000066367.41067.C2.
Rozen et al., "The two-dermal-flap umbilical transposition: a natural and aesthetic umbilicus after abdominoplasty", Plast. Reconstr. Surg., 2007, 119(7), pp. 2255-2262, DOI: 10.1097/01.prs.0000261037.69256.3e.
The Aesthetic Society, Aesthetic Plastic Surgery National Databank Statistics, 2019, 26 pages.
Vernon, "Umbilical transplantation upward and abdominal contouring in lipectomy", Am J Surg., 1957, 94, pp. 490-492.
Vidal et al., "Managing Complications in Abdominoplasty: A Literature Review", Arch. Plast. Surg., 2017, 44(5), pp. 457-468, DOI: 10.5999/aps.2017.44.5.457.
Villegas, "Lipoabdominoplasty: No. Supraumbilical Elevation Combined With Transverse Infraumbilical Plication", Video Description and Experience With 164 Patients, Aesthet Surg J., 2021, 41(5), pp. 577-594, DOI: 10.1093/asj/sjaa183.
Visconti et al., "Concepts in Navel Aesthetic: A Comprehensive Surface Anatomy Analysis", Aesthet Plast Surg., 2015, 39(1), pp. 43-50, DOI: 10.1007/s00266-014-0434-z.

* cited by examiner

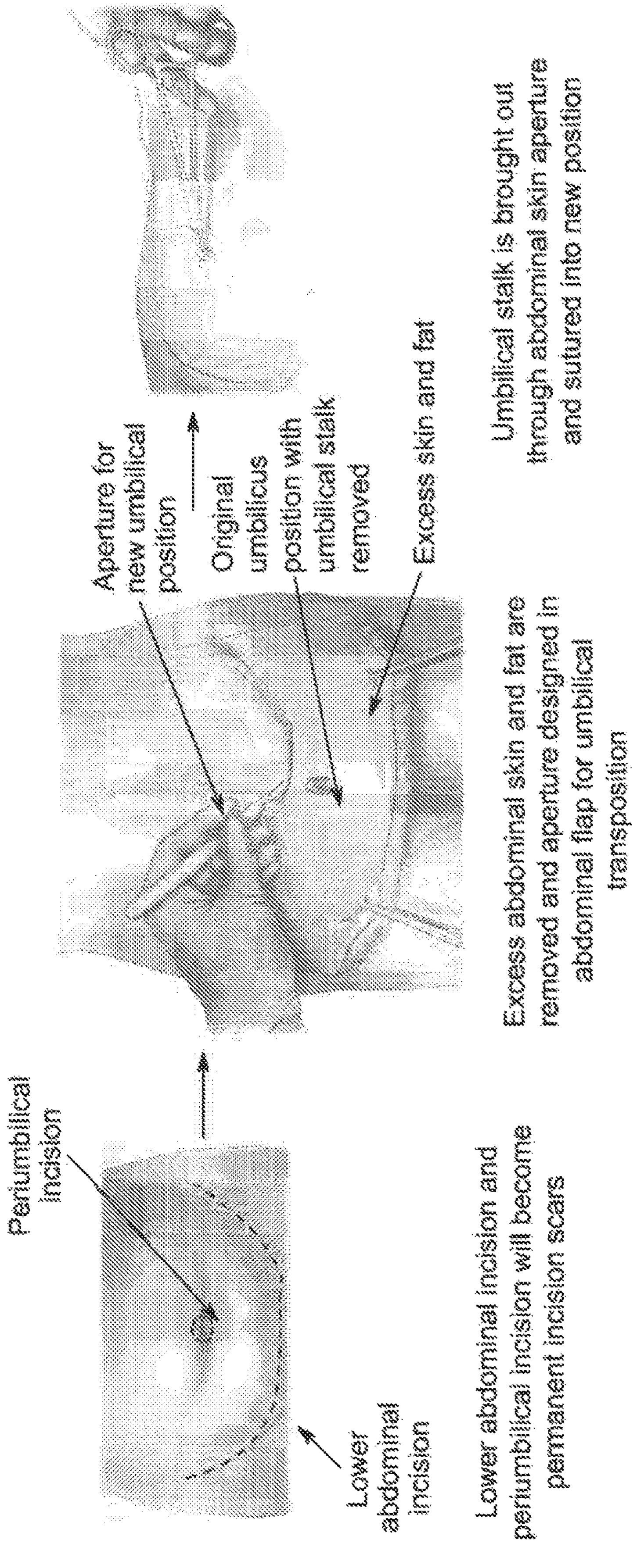
FIG. 1 - Prior Art

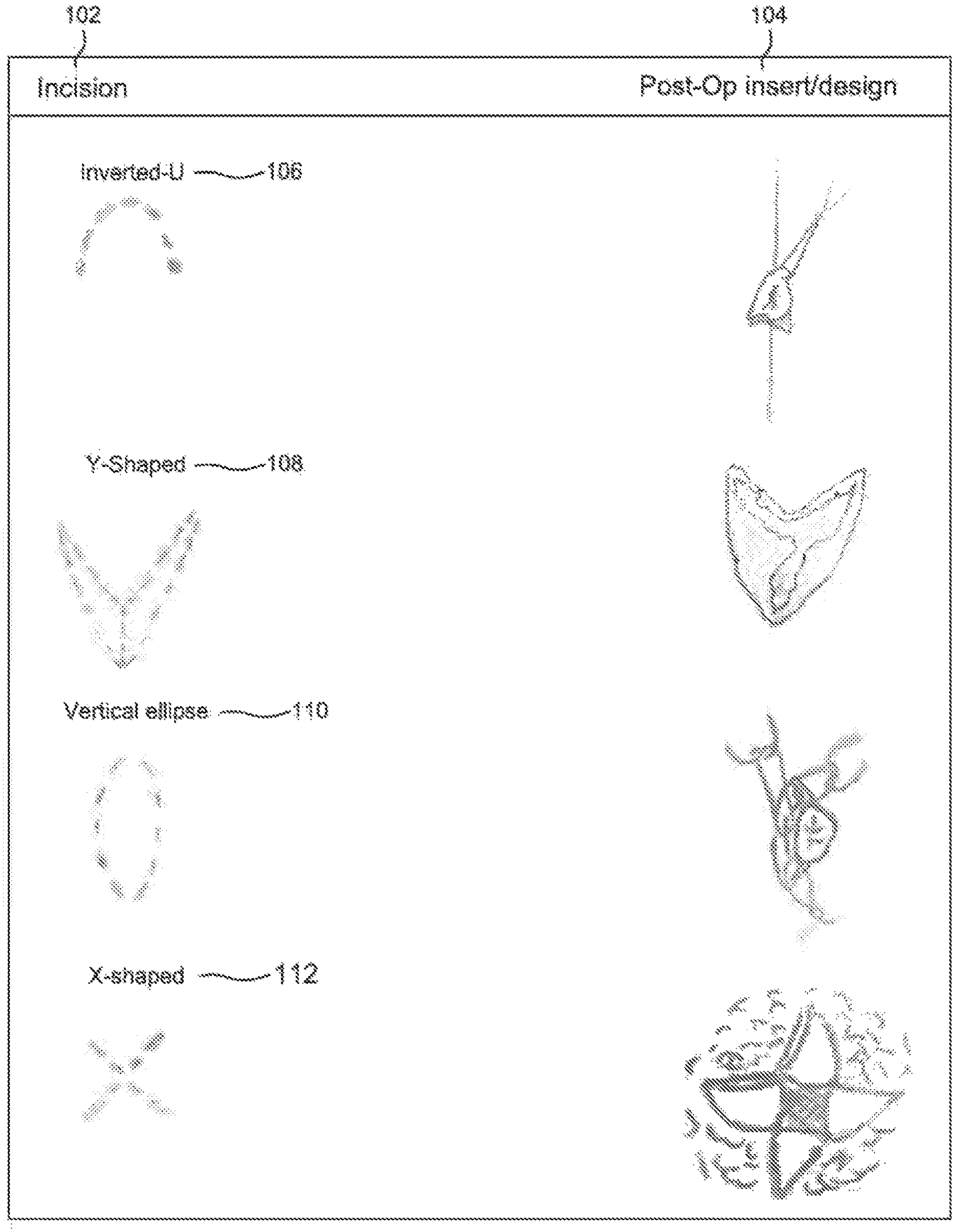
FIG. 2 - Prior Art

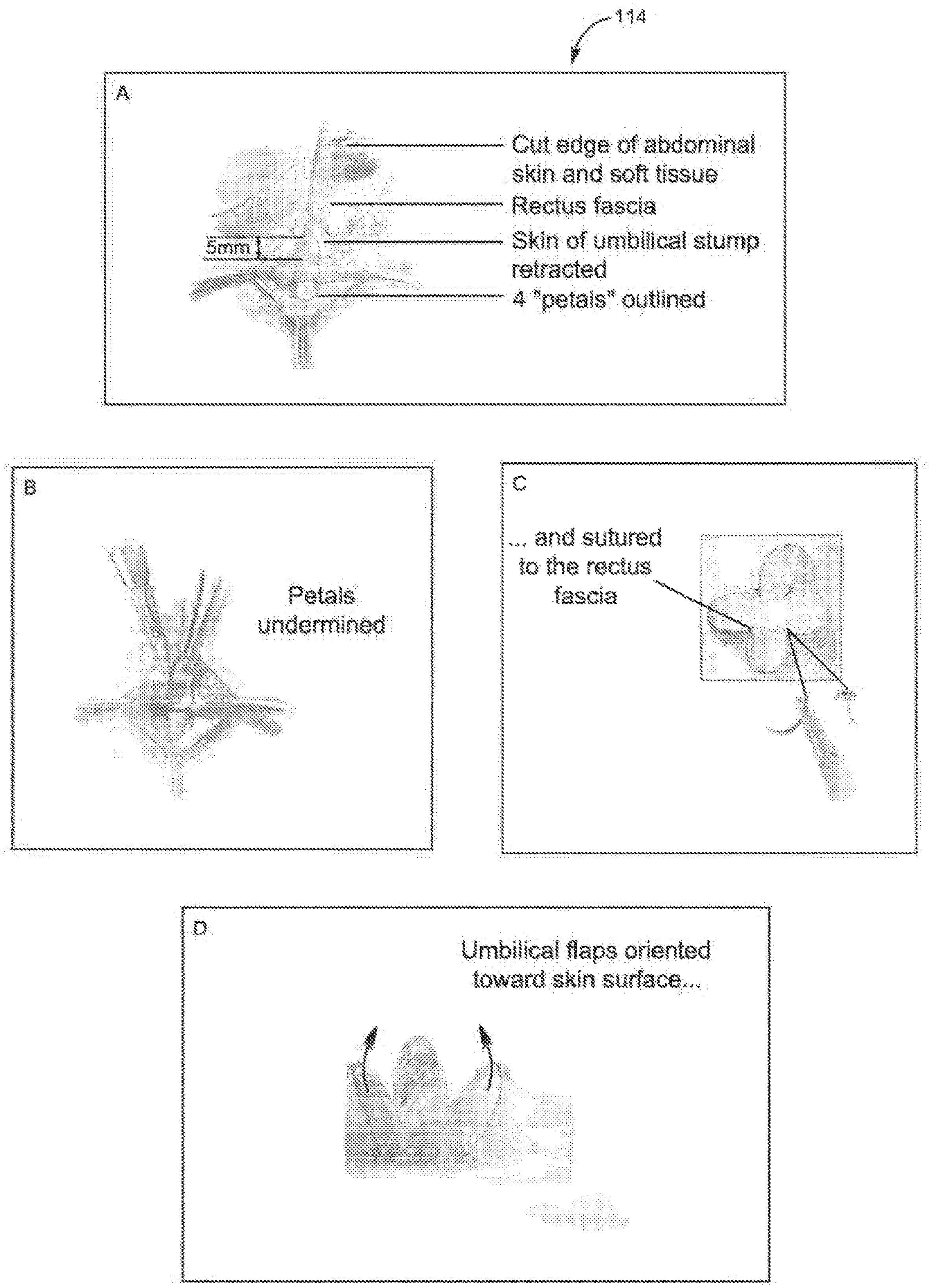
FIG. 3 - Prior Art

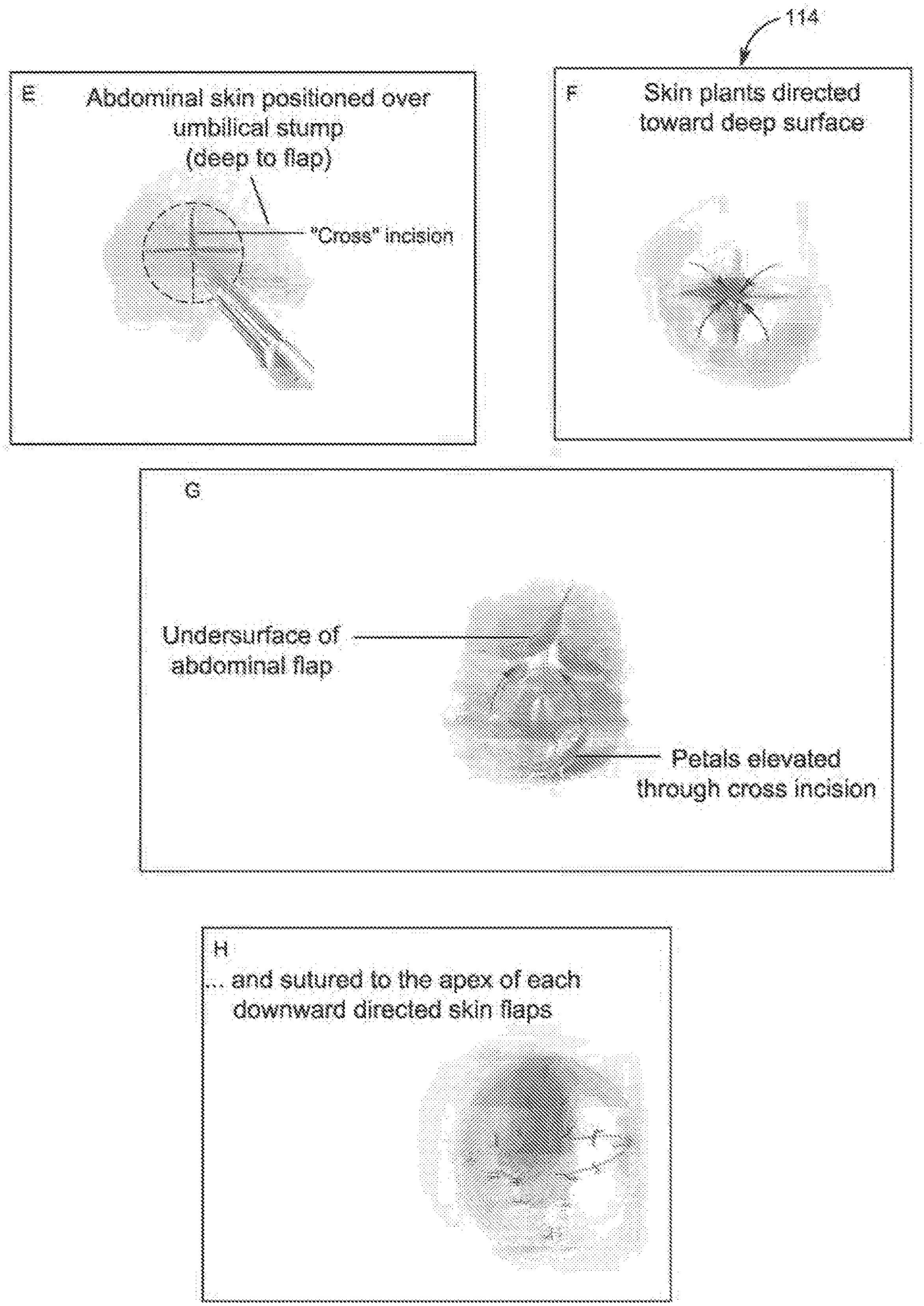
FIG. 4 - Prior Art

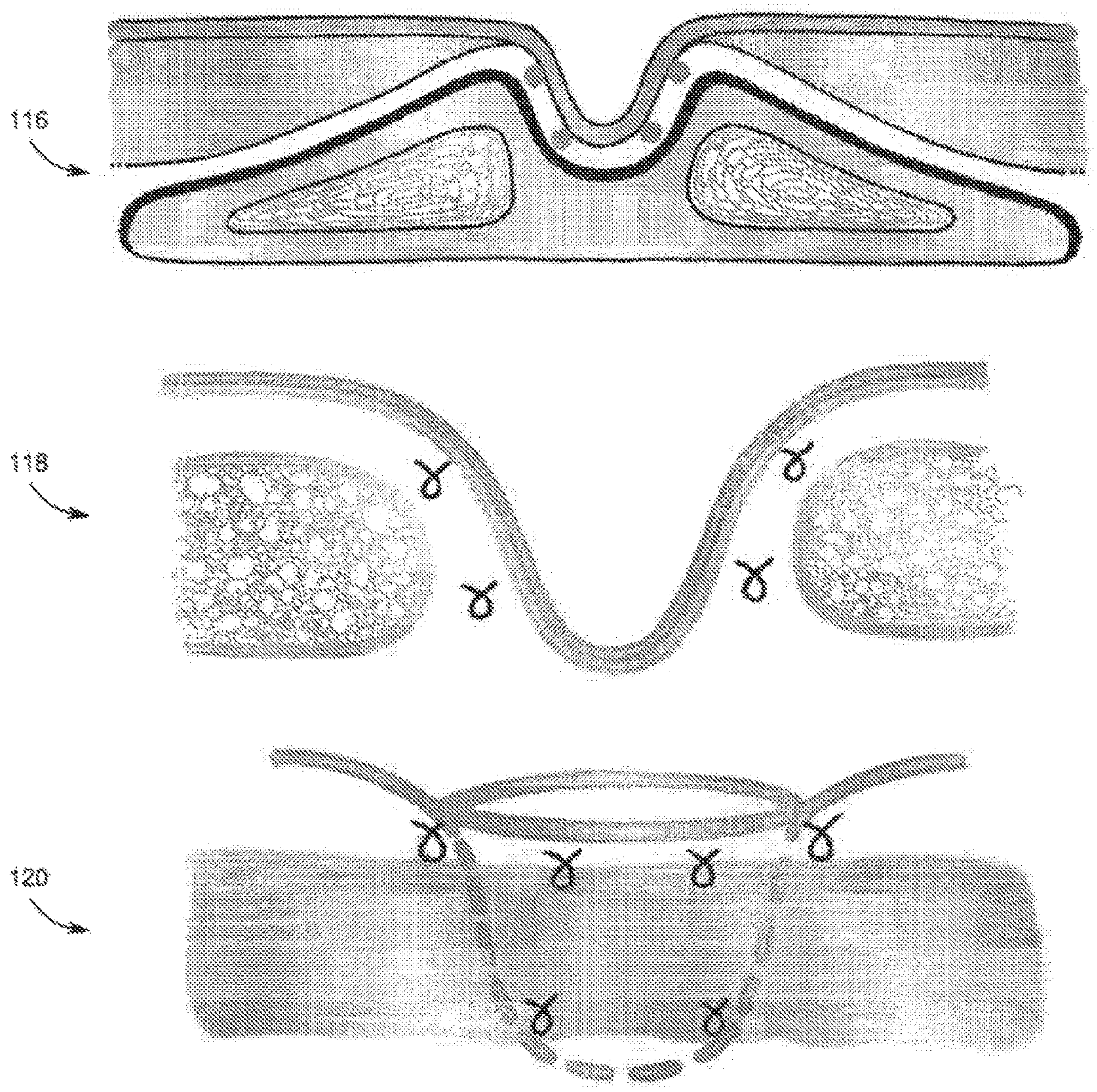
FIG. 5 - Prior Art

TISSUE EXPANDER DEVICE CREATING A SCARLESS NEO-UMBILICUS IN THE SURGICAL FIELD

This application claims priority of U.S. Provisional Application No. 63/327,819, filed Apr. 6, 2022, which is hereby incorporated by reference in its entirety as if fully set forth herein.

BACKGROUND

Abdominoplasty, colloquially known as "tummy tuck," is one of the most popular cosmetic surgical procedures in the world, with 140,381 cases performed in the United States and 924,031 cases globally in 2019 (Aesthetic Society Statistics, 2019) (ISAPS Statistics, 2019). The primary goals of an abdominoplasty are to improve the abdominal contour and waistline by removing excess skin and fat and tightening the musculofascial abdominal wall by repairing, if present, the rectus abdominis muscle separation ("rectus diastasis"). An important secondary goal is to aesthetically improve the belly button ("umbilicus"), which is the focal point of the abdomen. To best achieve these goals, the procedure has undergone a series of technical refinements since first described over a century ago (Kelly, 1910) (Vidal, P., et al., 2017) (Grazer, 1973) (Pitanguy, 1967) (Vernon, 1957).

The full abdominoplasty technique involves making incisions that ultimately result in two permanent scars: one linear incision extending from hip to hip ("lower abdominal incision"), which is needed to remove the excess abdominal skin and fat, and one circular incision around the umbilicus ("periumbilical incision"), which is needed to move the native umbilical stalk into its new position ("umbilical transposition"), as shown in FIG. 1. Briefly described, the abdominal skin and fat ("abdominal flap") are elevated off the underlying musculofascial abdominal wall leaving the umbilical stalk attached at its base. If a rectus diastasis is present, which is commonly the case among postpartum women, the medial muscle edges of the rectus abdominis muscles are sutured together at the midline ("rectus diastasis repair"). The abdominal flap is then pulled inferiorly, excess skin and fat are removed, and the lower abdominal incision is closed with sutures. At this point, the position of the native umbilicus still attached at its base to the abdominal wall is marked on the overlying abdominal skin and an opening, of which countless different incision designs are currently used by surgeons, is made through the abdominal flap. The umbilical stalk is brought out through this aperture and the umbilical skin and abdominal skin are sutured together in this new position ("umbilical transposition") to complete the procedure.

While the lower abdominal incision scar can easily be hidden from view in the bikini line, the periumbilical incision scar remains visible in any clothing that reveals the central abdomen. Moreover, studies have shown that the native umbilicus is most often not located in the midline (Rohrich, R. J., et al., 2003), and this anatomical asymmetry becomes more conspicuous after abdominoplasty due to a high tendency for poor scarring and outward migration of the scar onto the abdominal skin, two unsightly problems that are very difficult to prevent from occurring. Exacerbating matters, these cosmetic deformities are even more challenging to fully correct. As a corollary, the aesthetic appearance of the umbilicus after an abdominoplasty is the key to a beautiful surgical result and attaining a naturally-appearing umbilicus without any scar remains the "holy grail of abdominoplasty" (Boudreault, D., at al., 2019).

The two main umbilical repositioning techniques used in abdominoplasty include 1) "umbilical transposition" wherein the native umbilical stalk is brought out through and attached to an opening made in the abdominal skin and 2) "neo-umbilicoplasty" wherein the native umbilical stalk is excised along with the excess abdominal skin and fat and a "new" umbilicus is created by first incising and then securing abdominal skin down to the abdominal wall fascia and covering any raw tissue with skin grafts. For the umbilical transposition technique, numerous different abdominal skin incision designs have been described in the literature (Joseph, W. J., et al., 2016). Specifically, FIG. 2 depicts traditional incisions 102 and post-op inserts/designs 104 (Joseph, W. J., et al., 2016). The traditional incisions 102 include an inverted "U" shape 106, a "Y" shape 108, a vertical ellipse shape 110, or an "X"-shape 112. However, all these abdominal skin incisions are prone to healing with scar-related deformities including hypertrophic scars and keloids due to the high degree of tension on the incision, scar cicatrization causing umbilical stenosis due to the obligatory closed-loop of periumbilical incisions, and wound breakdown and dyschromia due to interrupting blood flow to the umbilical stalk, among others. These complications are even more prevalent among patients genetically predisposed to form poor scars (e.g., hypertrophic scars and keloids) as well as those with a higher body mass index (BMI) given that the degree of tension on the periumbilical skin edges is directly proportional to the thickness of the abdominal flap (Joseph, W. J., et al., 2016).

In an effort to minimize these complications, several innovative techniques have been published including the so-called "scarless" technique 114 (Mejia, J. D., 2019) (Reho, A., et al., 2019) depicted in FIG. 3 and FIG. 4 (Mejia, J. D., 2020). However, this technique is not truly scarless, with the scar just set closer to the umbilical base, and its application is limited to patients with a lower BMI and thinner abdominal flaps such that their abdominal skin can reach the umbilical base without excessive tension. Other innovations include neo-umbilicoplasty techniques as described by da Silva Júnior et al. and shown in FIG. 5 (da Silva Júnior, V. V., et al., 2017), and the TULUA technique (transverse plication, undermining halted at umbilicus, liposuction [without restrictions], umbilicoplasty with a skin graft, and abdominoplasty with low transverse scar localization) as described by Villegas (Villegas, F., 2021). However, while neo-umbilicoplasty techniques have the advantage of being able to position the neo-umbilicus at the most aesthetic location on the abdomen (i.e. not restricted by the location of the native umbilicus, which may be off-center), they are plagued by a paucity of abdominal skin to create the new umbilical stalk, leading to high degrees of tension and aforementioned negative sequelae when that abdominal skin is secured down to the abdominal wall fascia.

Ultimately, no umbilical repositioning technique is supported by the literature to consistently produce superior aesthetic results over another and thus the ideal technique has yet to be identified. The ideal umbilical repositioning technique would have three important features: 1) adequate abdominal skin to create a natural neo-umbilicus; 2) no visible scar; and 3) allow the surgeon to position the neo-umbilicus at the most aesthetic location on the abdomen irrespective of that of the native umbilicus. The present invention provides a novel tissue expander device that rather than incising or excising abdominal skin and bringing the native umbilical stalk, incision line, and future scar up to that aperture, the device can be placed at any location on the abdomen and stimulate growth of abdominal skin into a tubular form (or "skin tube"). Then, in a second procedure, this skin tube can be inverted and secured down to the abdominal wall fascia to create a natural-appearing neo-umbilicus in a truly scarless fashion. In addition to its use in abdominoplasty, this new neo-umbilicoplasty technique termed "scarless tissue expander-assisted neo-umbilicoplasty," can additionally be applied to any clinical situation in which a patient has no umbilicus, such as congenital abdominal wall deformities and acquired deformities from umbilical and ventral hernias and their associated reconstruction procedures.

Examples of Related Art Include

A first reference, WO 2014/175365 A1, describes a tissue expander that seeks to address issues with traditional tissue dilators, such as the fact that the skin cannot be sufficiently expanded if there is no hard tissue such as bone near the skin to be expanded. For example, in the abdomen, buttocks, or thigh, the soft tissue between the skin and bone is thicker than in the case of the jaw. When a traditional tissue dilator is installed on the back side of the skin of these parts, even if an attempt is made to inflate the bag-like body of the tissue dilator, the bag is received by the repulsive force of the skin. The body itself sinks into the inner side of the human body (soft tissue side) and the skin cannot be expanded reliably. To remedy this problem, the tissue expander of this reference is equipped with a base plate fastened to the back surface of skin, and a pouch body held between the back surface of skin and the base plate. The tissue expander is designed to expand the skin through dilation of the pouch body between the back surface of skin and the base plate. The pouch body can thereby be received and retained by the base plate, even in instances in which the expanding pouch body sinks towards the inside of the body due to repellant force of the skin. The pouch body can thereby be reliably distended out towards the skin side, and the skin can be expanded in a reliable manner.

There are several distinctions between the WO 2014/175365 A1 reference and the present invention. First, where the WO 2014/175365 A1 reference describes a rigid base plate attached to individual "protrusions" that interface with the undersurface of the skin, the present invention describes a rigid base plate, cylindrical sidewall, and anchoring ledge components constructed as a solid unit termed the body casing component. Second, the WO 2014/175365 A1 reference uses separate "foot-like" structures to connect the base plate to help the device adhere to the undersurface of the skin and provides the option of securing them with sutures. Distinctly, the present invention uses an anchoring ledge, which is a solid extension of the body casing and has different shapes and dimensions from those of the "foot-like" structures described in WO 2014/175365 A1, for suture fixation of the novel tissue expander device to the undersurface of the abdominal skin. Third, the WO 2014/175365 A1 reference describes a rigid base plate shape with four rounded corners and cuboid-shaped "bag-like body." Distinctly, the present invention has either a round or oval-shape rigid base plate-body casing component containing either an expander balloon component alone or an expander balloon component and a rigid closed-base thimble component.

Additionally, the WO 2014/175365 A1 reference does not describe use of a stencil for the precise positioning of the tissue expander as well as the exact locations for the suture placement, as are included in the present invention. Finally, the clinical purpose of the WO 2014/175365 A1 device is "for collecting from a human body the skin to be transplanted into a defective part in a regenerative operation of the defective part of the skin or soft tissue." Distinctly, the purpose of the device of the present invention is specifically to create a natural-appearing, scarless neo-umbilicus via tissue expansion.

A second reference, U.S. Pat. No. 4,984,585 A, describes a tissue expander for implantation in a patient to expand skin and mucosal tissue. The tissue expander comprises a low-profile construction facilitating implantation in the patient and which is effective to promote a more uniform expansion free of overfolds in the expansion envelope which have been present in prior art devices. The tissue expander comprises an envelope which is expansible by stretching. In one embodiment, the envelope is separably mounted on the base and the base can be cut by the surgeon to conform its general shape to the need of any given patient.

There are several distinctions between the U.S. Pat. No. 4,984,585 A reference and the present invention. The U.S. Pat. No. 4,984,585 A reference describes a tissue expander mounted on a rigid base "to exert a more uniform expansive force to the overlying tissue." However, this rigid base is not anchored in any way to the overlying skin and thus would not resist posterior expansion forces when expanded. Consequently, if positioned beneath the abdominal skin and expanded, this device described in U.S. Pat. No. 4,984,585 A would also expand posteriorly and potentially compress vital intraabdominal organs. Distinctly, the expander balloon component in the present invention is situated within a rigid body casing open only at its top where it is situated against and secured to the undersurface of the abdominal skin using sutures. As a result of this closed-bottom design, expansion of the expander balloon component exerts only upward forces against the skin with all posterior forces resisted by counterforces provided by the rigid body casing and its skin attachments, thereby optimizing safety.

A third reference, U.S. Pat. No. 10,792,121 B2, describes numerous embodiments of tissue expanders. More specifically, this reference describes a tissue expansion system that includes an implantable device and an external controller. The implantable device includes an expandable chamber, a rigid gas canister, and an antenna. The expandable chamber is defined by a posterior backing and a flexible anterior region secured to the posterior backing. The rigid gas canister has a compressed gas disposed therein. The rigid gas canister is disposed inside the expandable chamber that is defined by the posterior backing and the flexible anterior region. The rigid gas canister is secured relative to the posterior backing with a retention member that is directly attached to the posterior backing. The retention member extends around the rigid gas canister and at least partially surrounding the rigid gas canister. The retention member is flexible and has a hammock configuration within which the rigid gas canister is secured yet freely movable such that the rigid gas canister is not rigidly fixed to the retention member or the expandable chamber. The antenna is secured to the flexible anterior region and is sandwiched between two layers. The external controller is adapted to wirelessly communicate with the implantable device to cause the release of compressed gas from the rigid gas canister and into the expandable chamber, to thereby expand the expandable chamber. The external controller includes a computer executable method adapted to prevent at least one of the release of gas from the rigid gas canister more than three times within about a 24 hour period, or the release of more than 30 mL of gas within about 24 hours. Importantly, however, the present invention has a distinct design and utility from the device in the U.S. Pat. No. 10,792,121 B2 reference.

A fourth reference, U.S. Pat. No. 5,655,545 A, describes an intraoperative dissecting instrument in place of a "sharp or blunt dissection technique" typically used to "form a space or cavity or pocket" during breast augmentation surgery. A hollow tissue expander is then inserted into the incision to a point where a space or cavity or pocket is desired. Fluid is forced into the expander to cause it to expand and separate two layers of tissue to form the space or cavity or pocket. The expander can be used to dissect or create spaces: within subcutaneous fat; between skin and bone; skin and muscle or skin and fascia; between fat and bone; fat and muscle; fat and fascia; between peritoneum and muscle; peritoneum and fascia; between bladder and other tissue; between nerves and other tissue; between blood vessels and other tissues; or between muscle and other tissues. The tissue expander can also be used any place in the body where a surgeon could or would use other instruments to create spaces in, dissect or separate soft tissues. This use of a tissue expander to dissect tissue, create cavities or pockets, or separate layers of soft tissue can be done: under direct vision; under endoscopic vision; under X-ray vision; under blind conditions by manual palpitation; or any combination of the above. Importantly, however, the present invention has a distinct design and utility from the device of U.S. Pat. No. 5,655,545 A reference.

A fifth reference, Kadri, O. M., et al., Abdominoplasty Revision Using Tissue Expansion, *Aesthetic Plast. Surg., June* 2013, 37(3), Pages 538-40, describes that revision surgery after abdominoplasty may be necessary to improve contour, remove asymmetries, revise the umbilicus, and/or improve the scar. In one such case performed outside of the United States, the abdominoplasty resulted in an inappropriately high and unattractive scar with an elevated pubic hairline. The patient of this case presented 2 years after her initial surgery, and a scar-lowering procedure was performed with the assistance of tissue expansion. However, given that a traditional tissue expander device was utilized, the expansion forces were exerted in all directions including posteriorly against the deeper musculofascial abdominal wall. While expansion of overlying skin may occur safely and effectively with a traditional tissue expander device when placed on top of deeper structures that are rigid, such as the rib cage or calvarium, the musculofascial abdominal wall is soft and pliable, and consequently the posterior forces of the tissue expander device are transferred directly to the vital intra-abdominal organs. It is not unexpected, therefore, that the case series patient in the article experienced "reported pain, anorexia, and early satiety during the expansion process, which was attributed to pressure on the abdominal wall and stomach from the tissue expander." See, Page 4 of Kadri. Moreover, the high tissue pliability of the underlying deeper structures of the abdominal wall led to the tissue expander device's needing to be filled with a very large volume of fluid (3.5 liters). Nevertheless, the tissue expander stimulated sufficient abdominal skin growth during expansion and the scar was able to be successfully lowered and contour improved during a second procedure. The final result is exhibited in 1-month follow-up photographs (Kadri, 2013).

Distinctly, with the tissue expander device of the present invention, the expander balloon component is situated within a rigid body casing open only at its top where it is situated against and secured to the undersurface of the abdominal skin using sutures. As a result of this closed-bottom design, expansion of the expander balloon component exerts only upward forces against the skin with all posterior forces resisted by counterforces provided by the rigid body casing and its skin attachments, thereby optimizing safety. The authors' device also has a completely different design and utility from the present invention.

As such, though similar systems exist in the art, their design and utility are substantially different from those of the present invention, and the other inventions fail to solve all the problems taught by the present disclosure.

SUMMARY

The present invention and the example embodiments described herein relate to a novel tissue expander device for creation of a scarless, natural-appearing neo-umbilicus in the surgical field either when one does not exist, due to congenital or acquired causes, or when performing a full abdominoplasty procedure necessitating umbilical repositioning. Specifically, the present invention describes a novel tissue expander device that can be anchored to the undersurface of the abdominal skin at the most aesthetic location for an umbilicus, then afterward injected with saline to fill an expander balloon of the expander device in a postoperative setting over the course of days to weeks to grow a skin tube, and finally removed during a second procedure to invert the grown skin tube and attach it to the abdominal wall fascia as a neo-umbilicus.

A first example embodiment of a novel tissue expander device includes a base plate with a first end disposed opposite a second end, both ends of which are anchored internally to the undersurface of the abdominal skin. The first end of the base plate may include a round, oval, or elliptic shaped central area having a diameter (if circular) or an axis of reflection (if oval) or a long axis (if elliptic) less than about 3 cm long, although larger sizes and/or other shapes may alternatively be used. In embodiments, the shape of the base plate central area may form a depression in the base plate. The base plate further comprises a rigid body casing in the form of a circular, oval, or elliptic right cylinder sidewall having first and second ends that conform to the shape of the central area in the first end of the base plate. The sidewall is coupled at one end around the central area in the first end of the base plate, and is coupled at the other end to an anchoring ledge configured to be affixed to the undersurface of the abdominal skin using sutures. Further, the anchoring ledge may be circumferentially either continuous or discontinuous, and includes a plurality of paired apertures to receive sutures. Contained within the rigid body casing is an expander balloon that preferably measures less than about 4 cm in diameter, although larger sizes may alternatively be used. The second end of the base plate comprises an injection port that is ferromagnetic, which allows for magnet-assisted placement. The expander balloon is in fluid communication with the injection port via flexible tubing. The flexible tubing has a tight leak proof coupling at one end to the injection port, and a tight leak proof coupling at its other end to a fluid input port on the expander balloon. A diameter of the injection port may preferably be less than about 3 cm, although larger sizes may alternatively be used. An inner diameter of the connection tubing may preferably be less than about 4 mm, although larger sizes may alternatively be used.

To expand and grow the overlying abdominal skin into a tubular form in the postoperative setting, the ferromagnetic injection port is located using a magnet and its position marked and skin cleansed with betadine solution. Using a sterile technique, the injection port is percutaneously injected with saline to fill the expander balloon, which expands the overlying abdominal skin and stimulates its growth into a tubular form via physiologic processes called "mechanical and biological creep." Once the desired height and shape of this skin tube has been attained (which may be at least equal to the thickness of the abdominal flap or more), the novel tissue expander device is removed in a second procedure. The skin tube formed may then be inverted and secured down to the abdominal wall fascia as a scarless neo-umbilicus.

Alternatively, the tissue expander device may be placed during the initial surgery, and saline injected at that time to immediately stretch the skin into a preferred configuration. This occurs predominantly via the "mechanical creep" physiologic process, as opposed the "biologic creep" process mentioned above, which takes much longer (typically days to weeks). Although the skin may be stretched in this way only a relatively small amount without being damaged, it may be possible to create enough laxity in the skin for it to be distended into at least a partial skin tube that can be inverted and secured to the native umbilical stalk/base. Although this would not create a neo-umbilicus per se, it does provide a way to hide the resulting scar deeper than usual inside the patient's native umbilicus, which is commonly left attached to the abdominal wall during the umbilical transposition technique. Such umbilical transposition may be performed, for example, in abdominoplasty, as was noted previously.

A second example embodiment is a novel tissue expander device with an external injection port ("external port"). Similar to the first embodiment, a rigid body casing is anchored to the undersurface of the abdominal skin in a pre-expansion state. However, in contrast to the first embodiment, the flexible tubing is longer, and exits the internal surgical site through an incision in the central lower abdomen. As in the first embodiment, the flexible tubing attaches at one end to an injection port, now secured using sutures to the external surface of the abdominal skin. The flexible tubing attaches at its other end to a fluid input port on the expander balloon. A diameter of the injection port may preferably be less than about 3 cm, and an inside diameter of the tubing may be less than about 4 mm, although larger sizes may alternatively be used for either or both. Because of its external location, the injection port in this embodiment does not require a magnet for positioning, and does not require percutaneous injection for access. Similar to the first embodiment, injections of saline into the injection port fill the expander balloon and expand and grow the overlying abdominal skin into a tubular form that becomes the neo-umbilicus.

A third example embodiment of the present invention is similar to the first embodiment with the addition of a rigid closed-base thimble component situated between the expander balloon and abdominal skin. A fourth embodiment of the present invention is similar to the second embodiment with the addition of the rigid closed-base thimble component.

Upon saline injection into the external injection port, in contrast to the first and second embodiments, in the third and fourth embodiments as the expander balloon fills it now pushes, not directly against the undersurface of the abdominal skin, but instead against the undersurface of the closed-base thimble component. The closed-base thimble component pushes against the overlying abdominal skin, causing it to expand and grow into a tubular form that becomes the neo-umbilicus.

It is to be understood that the foregoing general description and the following detailed description are exemplary and explanatory but not limiting, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings:

FIG. 1 depicts a prior art schematic diagram depicting a full abdominoplasty technique and the locations of the lower abdominal and periumbilical incisions that ultimately result in two permanent scars, according to at least some embodiments disclosed herein.

FIG. 2 depicts a prior art schematic diagram depicting the many incision designs used in current abdominal transposition techniques and their post-operative insert and design, according to at least some embodiments disclosed herein.

FIG. 3 depicts a prior art schematic diagram depicting surgical steps in a "scarless" technique, according to at least some embodiments disclosed herein.

FIG. 4 depicts is a prior art schematic diagram depicting additional surgical steps in a "scarless" technique and is a continuation of FIG. 3, according to at least some embodiments disclosed herein.

FIG. 5 depicts a prior art schematic diagram depicting surgical steps in a neo-umbilicoplasty technique, according to at least some embodiments disclosed herein.

DETAILED DESCRIPTION

Figure 6A:
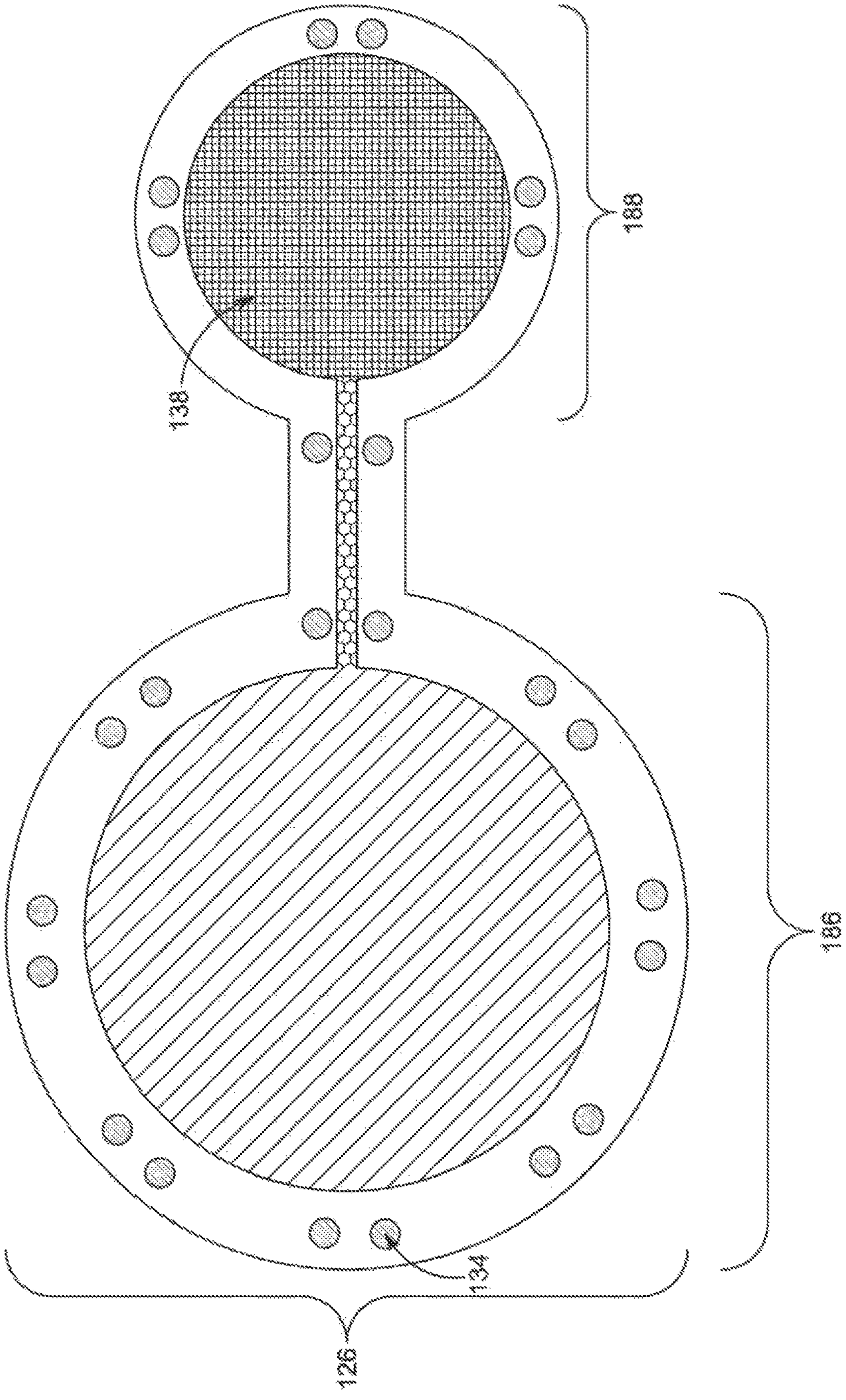
FIG. 6A depicts an overhead view of a schematic diagram portraying a novel tissue expander device with a round-shaped base comprising an internal port in a pre-expansion state, according to at least some embodiments disclosed herein.

Example embodiments of the present invention will now be described with reference to the drawings, in which identical elements in the various figures are identified with the same reference numerals. These embodiments are provided by way of explanation of the present invention, which is not intended to be limited thereto. In fact, those of ordinary skill in the art may appreciate upon reading the present specification and viewing the present drawings that various modifications and variations can be made thereto.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described herein. The materials, methods, and examples are illustrative only and not intended to be limiting. Other features of the disclosure are apparent from the following detailed description and the claims.

As used herein, the singular forms “a,” “an,” and “the,” are intended to include the plural forms as well, unless the context clearly indicates otherwise.

The phrase "and/or," as used herein in the specification and in the claims, should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

As explained herein, an abdominoplasty is a cosmetic surgery procedure that improves the abdominal contour and waistline by removing excess skin and fat and tightening the musculofascial abdominal wall by repairing, if present, the rectus diastasis. The full abdominoplasty technique involves making incisions that ultimately result in two permanent scars: a linear lower abdominal incision and a periumbilical incision, the latter of which is needed for umbilical transposition. While the lower abdominal incision scar can easily be hidden from view in the bikini line, the periumbilical incision scar remains visible in any clothing that reveals the central abdomen. Moreover, due to high tension, a closed-loop incision, and interrupted blood flow, this periumbilical incision is prone to developing significant cosmetic deformities that include hypertrophic scars and keloids, scar cicatrization causing umbilical stenosis, and wound breakdown and dyschromia, all of which are very challenging to fully correct. As a corollary, the aesthetic appearance of the umbilicus after an abdominoplasty is the key to a beautiful surgical result and attaining a natural-appearing umbilicus without any scar remains the "holy grail of abdominoplasty" and the ideal technique has yet to be identified.

To remedy these aforementioned problems in the field, the present invention provides a novel tissue expander device that, rather than incising or excising abdominal skin and bringing the native umbilical stalk, incision line, and future scar up to that aperture, the novel tissue expander device can be used to create a natural-appearing scarless neo-umbilicus. Specifically, the novel tissue expander device of the present invention includes a rigid body casing comprising a base plate. The base plate has a first end disposed opposite a second end. The first end of the base plate may be round or oval in shape. The base plate also includes a circular, oval, or elliptic cylinder sidewall and an anchoring ledge at the top where the novel tissue expander device is affixed to the undersurface of the abdominal skin using sutures.

Contained within this body casing is a tissue expander or an expandable balloon that is connected to an injection port with connection tubing. This injection port can be located internally beneath the abdominal skin or externally on top of it, and its injection with saline causes the expander balloon to fill. As a result of this closed-bottom design, expansion of the expander balloon component exerts only upward forces against the skin with all posterior forces resisted by counterforces provided by the rigid body casing and its skin attachments, thereby optimizing safety.

In the first and second embodiments of the present invention, saline injections fill the expander balloon and expansion occurs directly against the undersurface of the abdominal skin. In the third and fourth embodiments of the present invention, saline injections expand the expander balloon against the undersurface of a rigid closed-base thimble, which, in turn, expands against the undersurface of the abdominal skin. Once the tissue expansion has attained a skin tube of desired height (about equal to the thickness of the abdominal flap), the novel tissue expander device is removed in a second procedure and the skin tube inverted and secured down to the abdominal wall fascia as a scarless neo-umbilicus. Additionally, this ability to create a neo-umbilicus without an incision and thus without a scar means that scar-related deformities inherent in current umbilical repositioning techniques may be altogether avoided. Finally, the novel tissue expander device of the present invention can be used to create a scarless neo-umbilicus at the most aesthetic location on the abdomen irrespective of the location of the native umbilicus, which may not be located on the midline.

In general, the tissue expander or the expandable balloon, the connection tubing, and the injection port comprise a silicone elastomer or similarly flexible biocompatible material. Further, in general the body casing and the rigid closed-base thimble component comprise a rigid biocompatible plastic or similar material.

In general, the body casing, the tissue expander or the expandable balloon, and the rigid closed-base thimble component each comprise a diameter of at least approximately 3 cm. Moreover, the connection tubing comprises a diameter of at least approximately 4 mm. Additionally, the injection port comprises a diameter of at least approximately 3 cm. Further, the anchoring ledge extends at least approximately 8 mm out from the cylindrical sidewall. It should be appreciated that these materials and dimensions are being provided for illustrative purposes only and other materials and dimensions are contemplated.

Example Embodiments of the Invention

Four embodiments of a novel tissue expander device 126 are described herein. The novel tissue expander device 126 may be used for the creation of a scarless, natural-appearing neo-umbilicus in the surgical field either when one does not exist, due to congenital or acquired causes, or when performing a full abdominoplasty necessitating umbilical repositioning. Specifically, the novel tissue expander device 126 can be anchored to the undersurface of the abdominal skin at the most aesthetic location for an umbilicus, filled with saline injections in the postoperative setting over the course of days to weeks to expand and grow a skin tube, and removed during a second procedure to allow for skin tube inversion and attachment to the abdominal wall fascia to complete the neo-umbilicoplasty.

First Embodiment

Figure 6B:
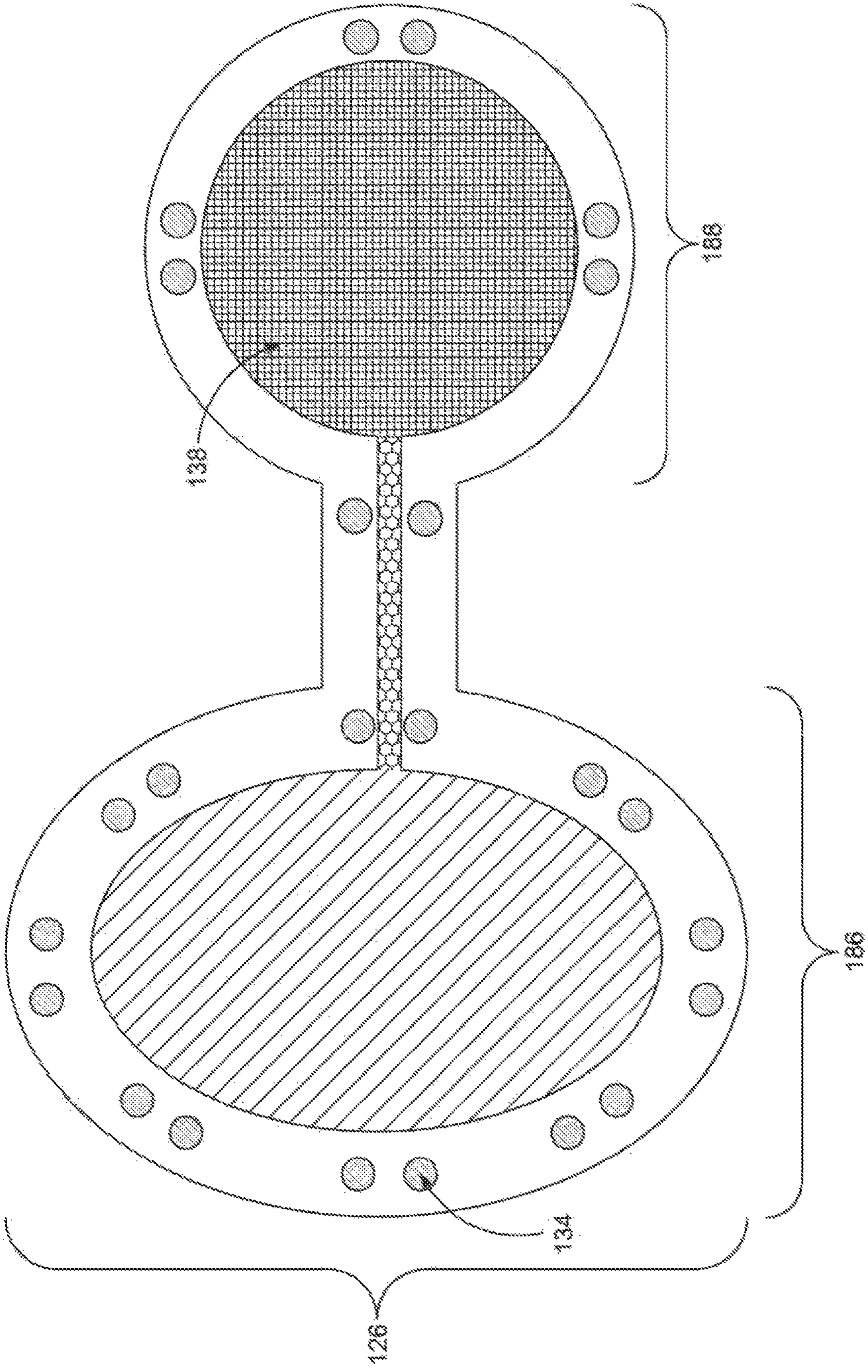
FIG. 6B depicts an overhead view of a schematic diagram portraying a novel tissue expander device with an oval-shaped base comprising an internal port in a pre-expansion state, according to at least some embodiments disclosed herein.
Figure 6C:
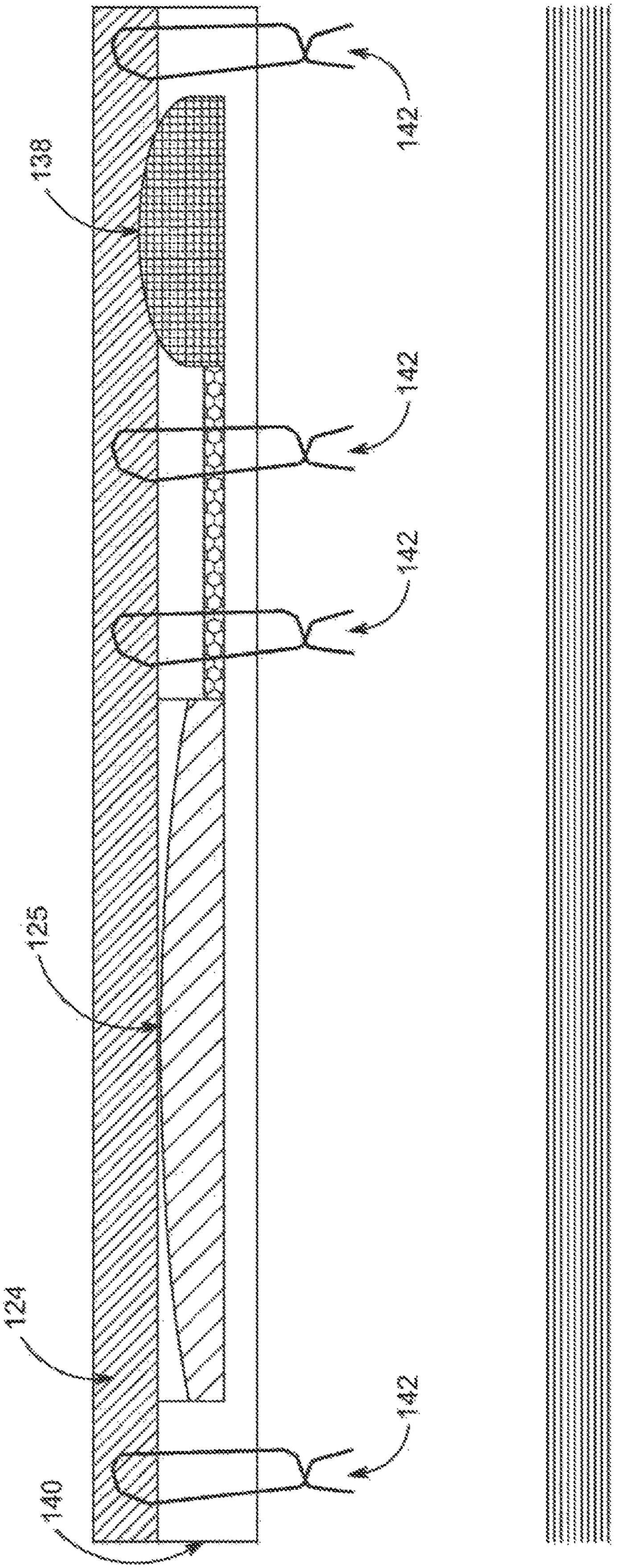
FIG. 6C depicts a side view of a schematic diagram portraying a novel tissue expander device comprising an internal port in a pre-expansion state, according to at least some embodiments disclosed herein.
Figure 6D:
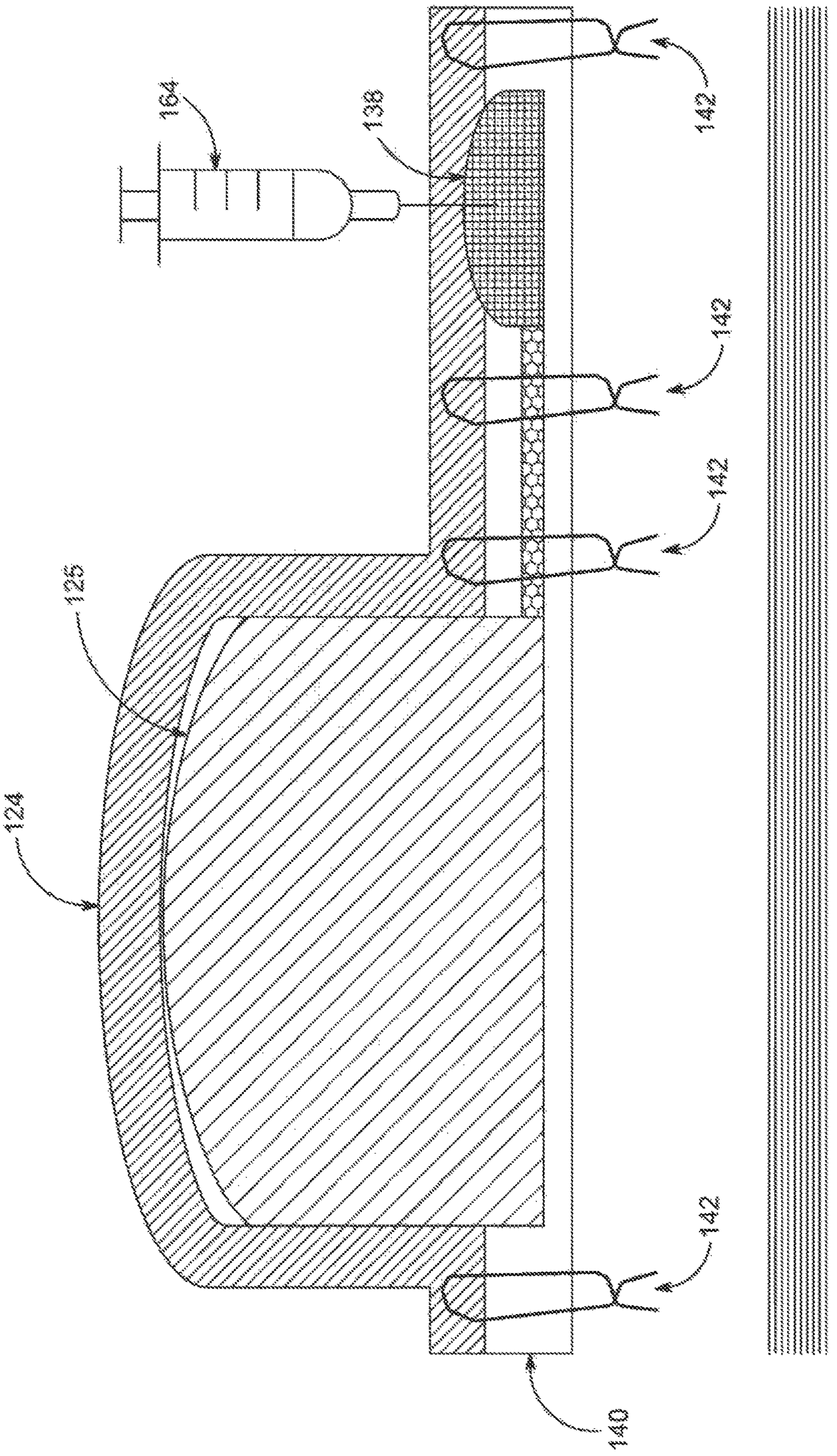
FIG. 6D depicts a side view of a schematic diagram portraying a novel tissue expander device comprising an internal port in a post-expansion state after a saline injection is received by an injection port, according to at least some embodiments disclosed herein.

A first embodiment of the novel tissue expander device 126 comprises an internal injection port 138, as shown in FIG. 6A, FIG. 6B, FIG. 6C, and FIG. 6D. Specifically, FIG. 6A depicts an overhead view of a schematic diagram portraying the novel tissue expander device 126 with a round-shaped base comprising the internal injection port 138 in a pre-expansion state and FIG. 6B depicts an overhead view of a schematic diagram portraying the novel tissue expander device 126 with an oval-shaped base comprising the internal injection port 138 in pre-expansion state. FIG. 6C depicts a side view of a schematic diagram portraying the novel tissue expander device 126 comprising the internal injection port 138 in a pre-expansion state and FIG. 6D depicts a side view of a schematic diagram portraying the novel tissue expander device 126 comprising the internal injection port 138 in a post-expansion state after a saline injection 164 is received by the internal injection port 138.

The novel tissue expander device 126 of the first embodiment includes a rigid body casing comprising a rigid base/base plate 140 (of FIG. 6C and FIG. 6D). The rigid base/base plate 140 includes a cylindrical sidewall and an anchoring ledge at the top where the novel tissue expander device 126 is affixed to the undersurface of the abdominal skin 124 using sutures 142. In general, and as shown in FIG. 6A and FIG. 6B, the rigid base/base plate 140 has a first end 186 disposed opposite a second end 188. The first end 186 may be round in shape (as shown in FIG. 6A) or oval in shape (as shown in FIG. 6B). Moreover, FIG. 6A and FIG. 6B depict apertures 134 disposed on a circumference of the rigid base/base plate 140. The individual apertures 134 may each receive deep dermal stitches 142 with interposing plastic to be tied over.

Contained within this rigid body casing is a tissue expander or an expandable balloon 125 (as shown in FIG. 6C and FIG. 6D) that is connected to the internal injection port 138 with connection tubing. In this first embodiment, the internal injection port 138 is located internally beneath the abdominal skin 124 and its injection with saline causes the expandable balloon 125 filling.

As a result of this closed-bottom design, expansion of the expandable balloon 125 exerts only upward forces against the abdominal skin 124 with all posterior forces resisted by counterforces provided by the rigid body casing and its skin attachments, thereby optimizing safety. Specifically, as shown in FIG. 6D, the saline injection 164 fills the expandable balloon 125 and expansion occurs directly against the undersurface of the abdominal skin 124. Once the tissue expansion has attained a skin tube of desired height (about equal to the thickness of the abdominal flap), the novel tissue expander device 126 is removed in a second procedure and the skin tube is inverted and secured down to the abdominal wall fascia as a scarless neo-umbilicus.

Second Embodiment

Figure 7A:
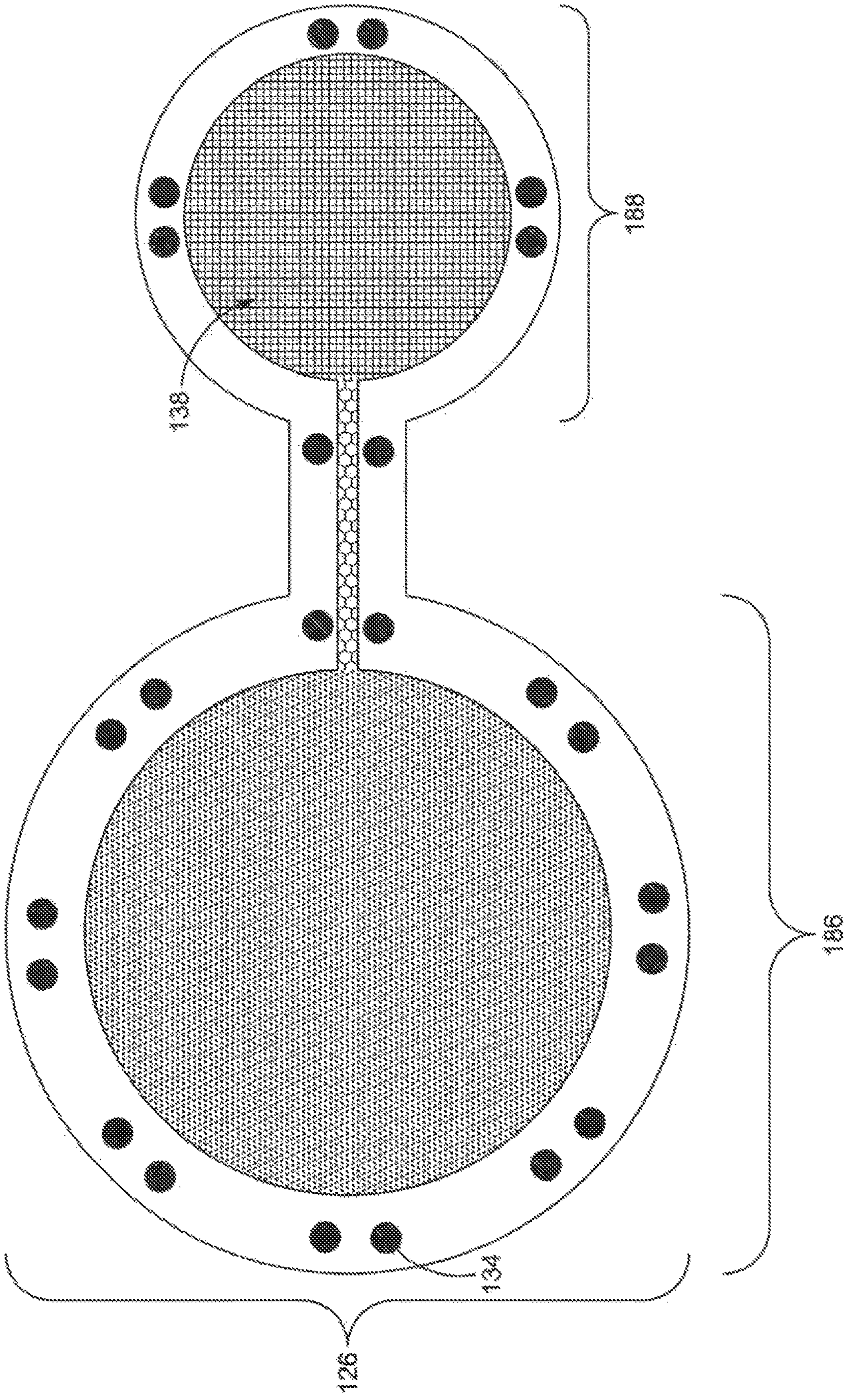
FIG. 7A depicts an overhead view of a schematic diagram portraying a novel tissue expander device with a round-shaped base comprising an internal port and a rigid closed-base thimble component in a pre-expansion state, according to at least some embodiments disclosed herein.
Figure 7B:
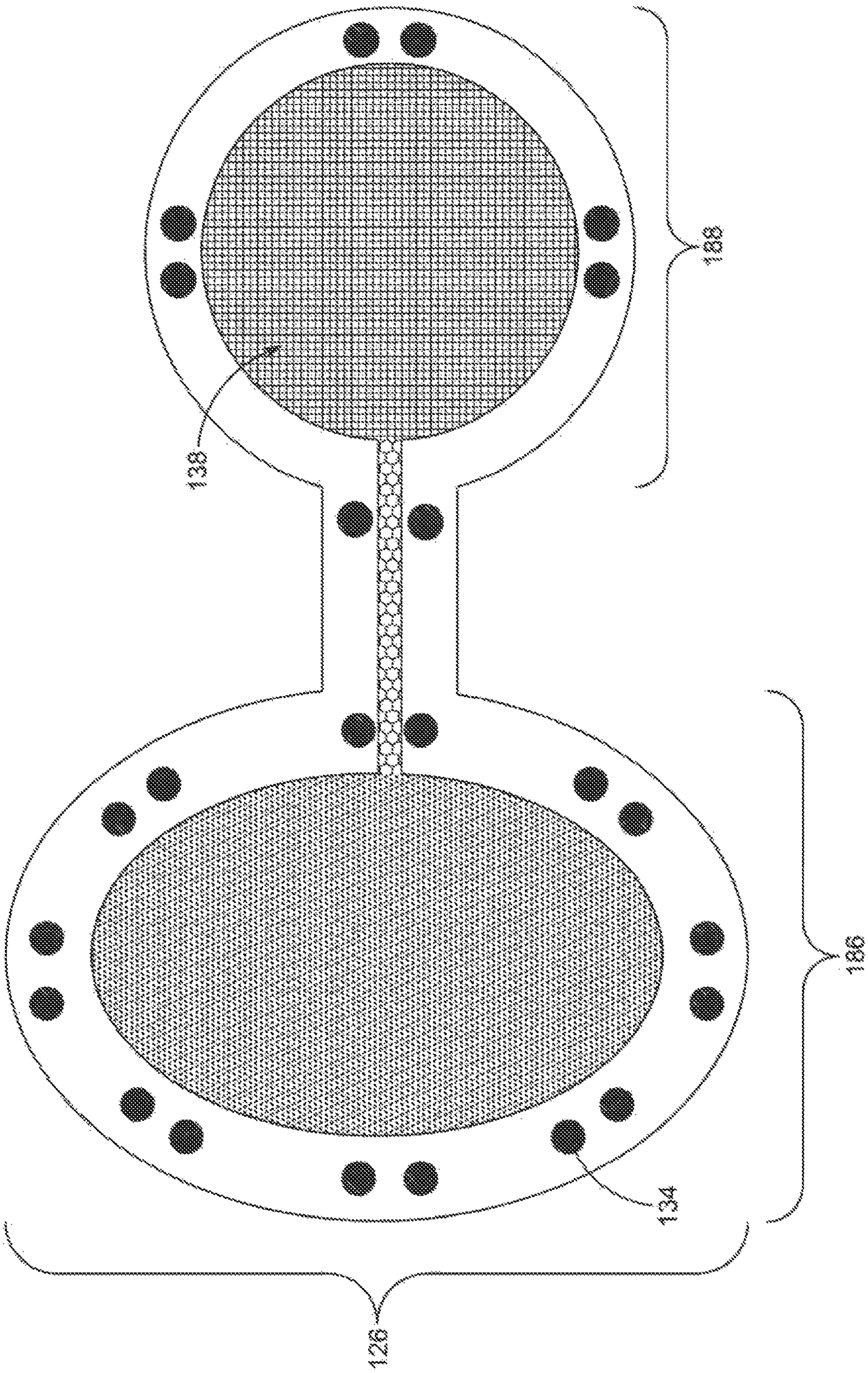
FIG. 7B depicts an overhead view of a schematic diagram portraying a novel tissue expander device with an oval-shaped base comprising an internal port and a rigid closed-base thimble component in a pre-expansion state, according to at least some embodiments disclosed herein.
Figure 7C:
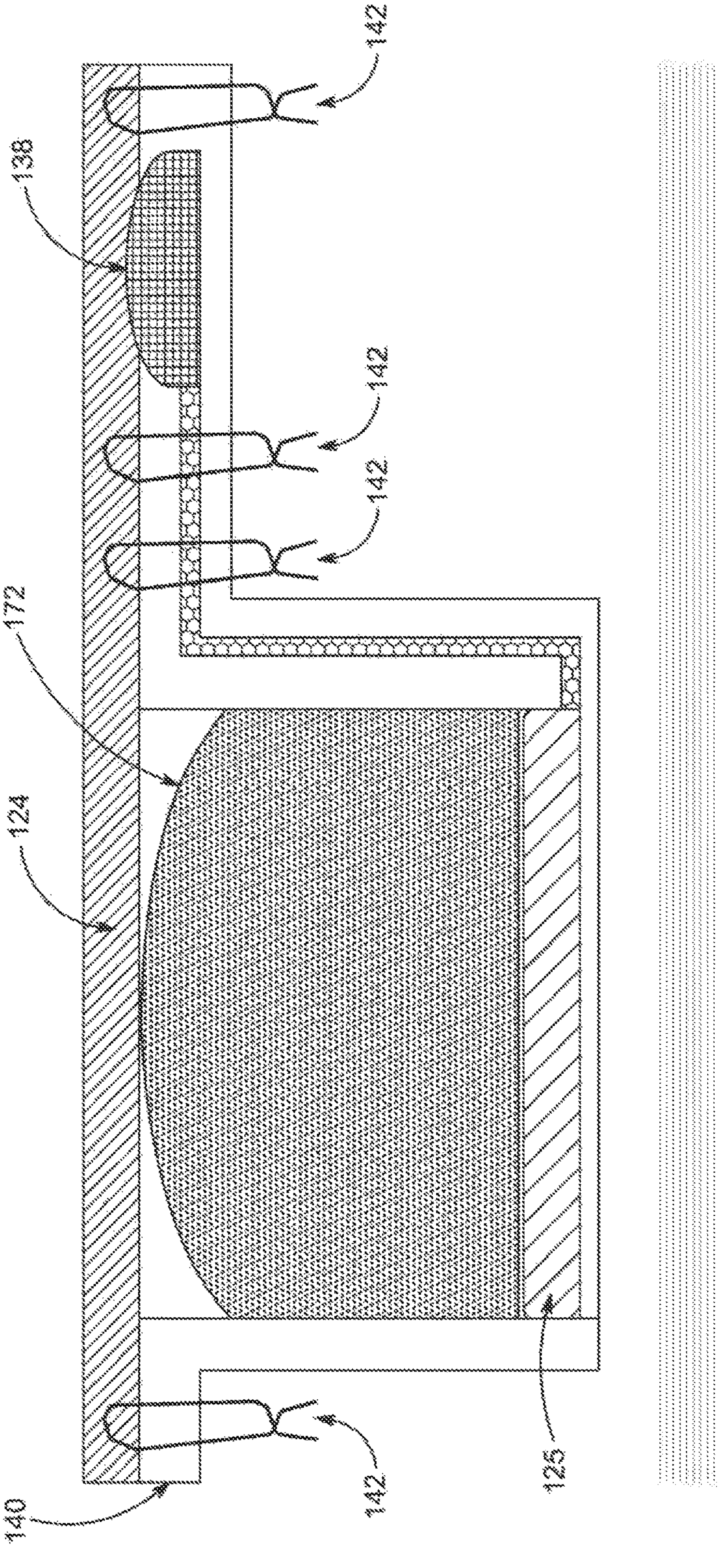
FIG. 7C depicts a side view of a schematic diagram portraying a novel tissue expander device comprising an internal port and a rigid closed-base thimble component in a pre-expansion state, according to at least some embodiments disclosed herein.
Figure 7D:
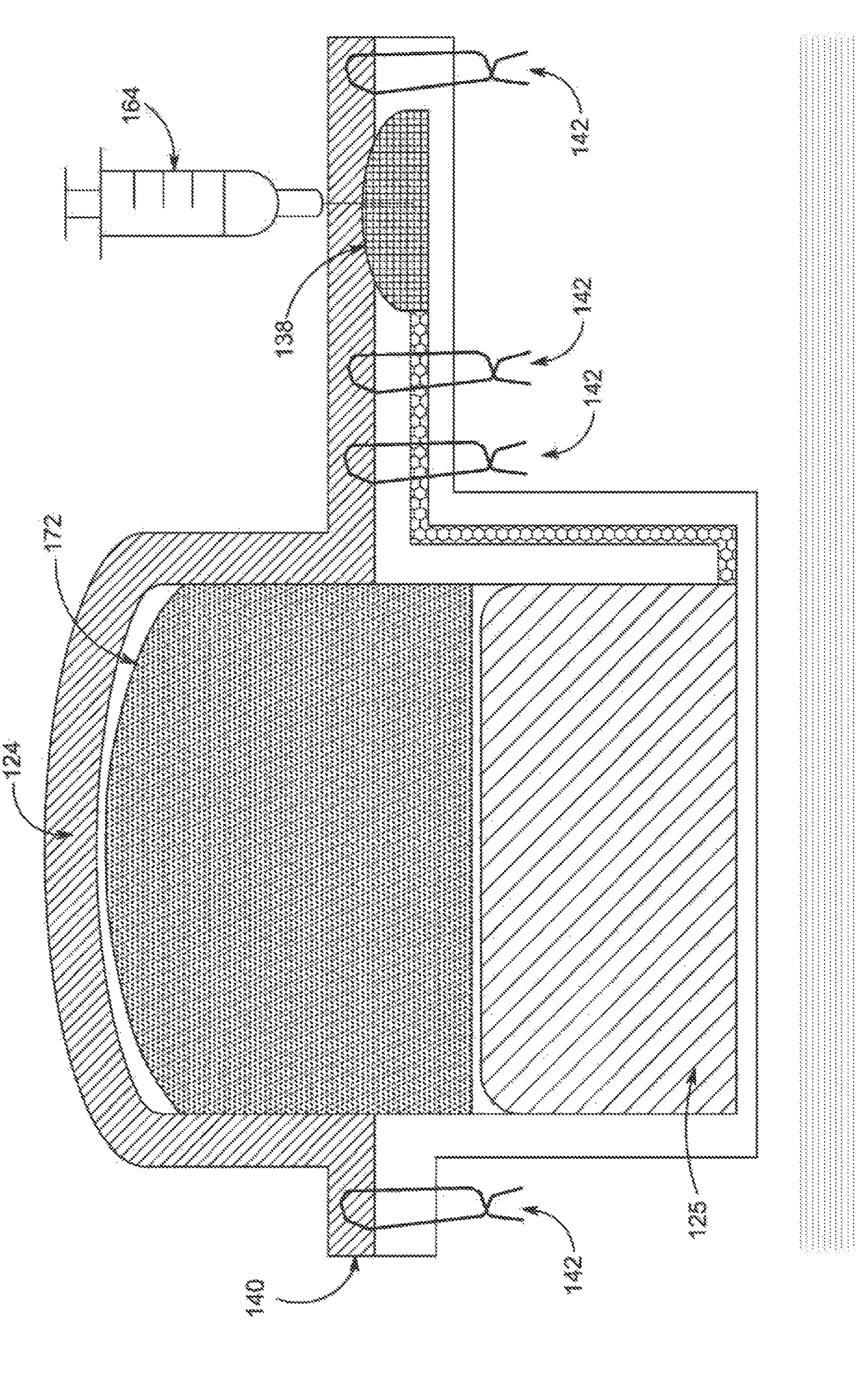
FIG. 7D depicts a side view of a schematic diagram portraying a novel tissue expander device comprising an internal port and a rigid closed-base thimble component in a post-expansion state after a saline injection is received by an injection port, according to at least some embodiments disclosed herein.

A second embodiment of the novel tissue expander device 126 comprises the internal injection port 138 and a rigid closed-base thimble component 172, as shown in FIG. 7A, FIG. 7B, FIG. 7C, and FIG. 7D. Specifically, FIG. 7A depicts an overhead view of a schematic diagram portraying the novel tissue expander device 126 with a round-shaped base comprising the internal injection port 138 and the rigid closed-base thimble component 172 in a pre-expansion state and FIG. 7B depicts an overhead view of a schematic diagram portraying the novel tissue expander device 126 with an oval-shaped base comprising the internal injection port 138 and the rigid closed-base thimble component 172 in a pre-expansion state. FIG. 7C depicts a side view of a schematic diagram portraying the novel tissue expander device 126 comprising the internal injection port 138 and the rigid closed-base thimble component 172 in a pre-expansion state and FIG. 7D depicts a side view of a schematic diagram portraying the novel tissue expander device 126 comprising the internal injection port 138 and the rigid closed-base thimble component 172 in a post-expansion state after the saline injection 164 is received by the internal injection port 138.

The configuration of the second embodiment of the novel tissue expander device 126 is substantially similar to the configuration of the first embodiment of the novel tissue expander device 126, with the exception that the second embodiment of the novel tissue expander device 126 additionally includes the rigid closed-base thimble component 172. As shown in FIG. 7D, the saline injection 164 fills the internal injection port 138 and expansion of the expandable balloon 125 occurs against an undersurface of the rigid closed-base thimble component 172, which, in turn, expands against the undersurface of the abdominal skin 124 of the patient 150. Once the tissue expansion has attained a skin tube of desired height (about equal to the thickness of the abdominal flap), the novel tissue expander device 126 is removed in a second procedure and the skin tube is inverted and secured down to the abdominal wall fascia as a scarless neo-umbilicus.

Third Embodiment

Figure 8A:
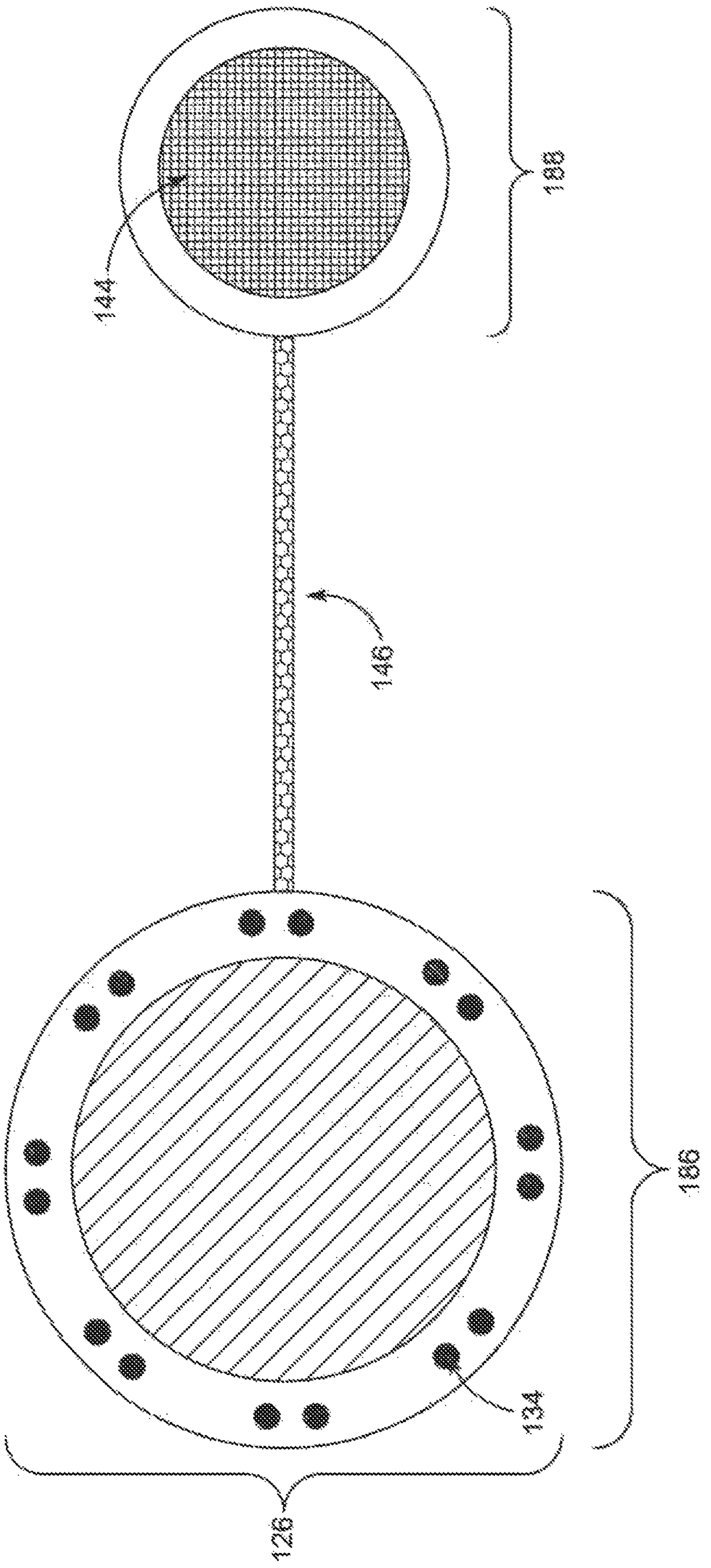
FIG. 8A depicts an overhead view of a schematic diagram portraying a novel tissue expander device with a round-shaped base comprising an external port in a pre-expansion state, according to at least some embodiments disclosed herein.
Figure 8B:
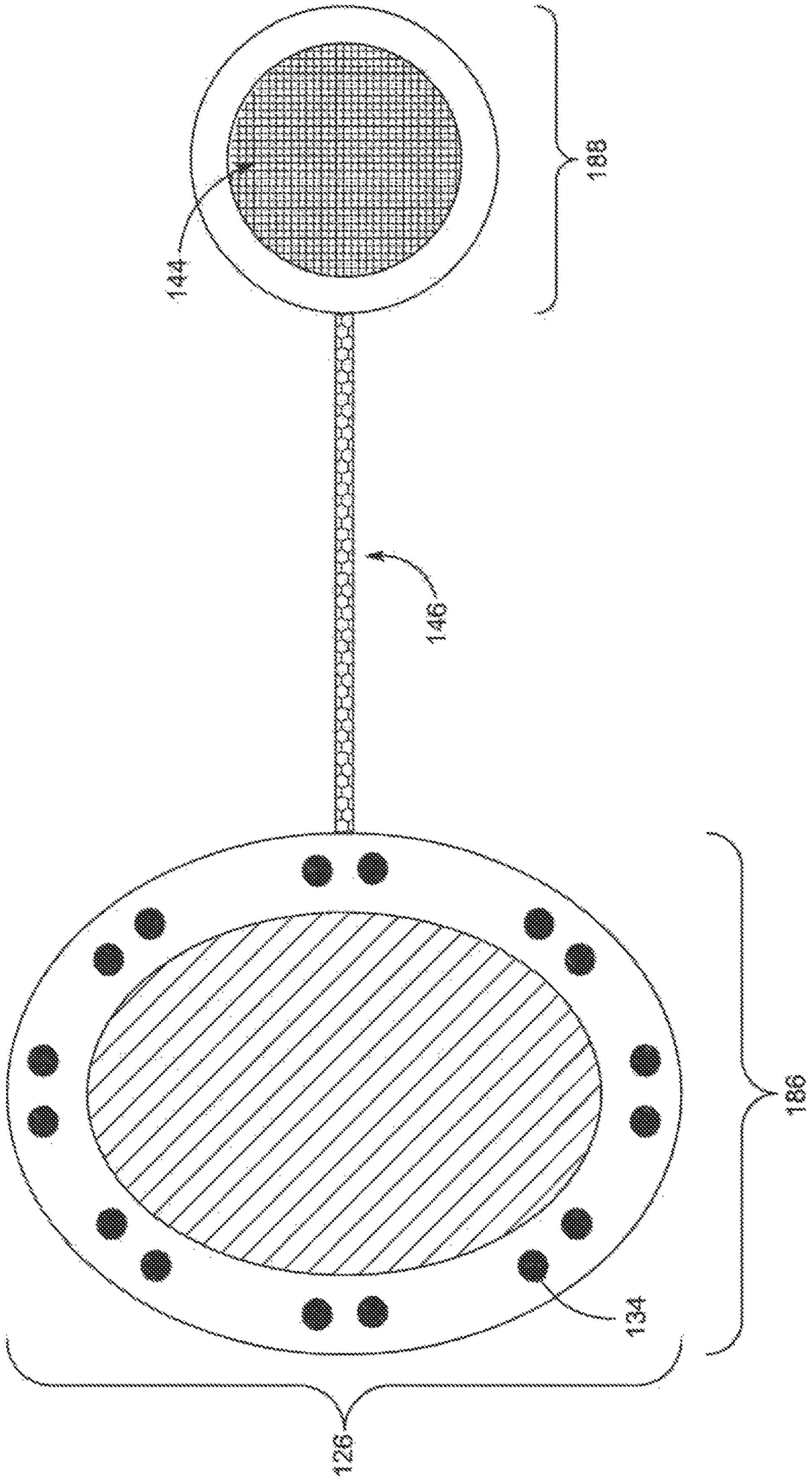
FIG. 8B depicts an overhead view of a schematic diagram portraying a novel tissue expander device with an oval-shaped base comprising an external port in a pre-expansion state, according to at least some embodiments disclosed herein.
Figure 8C:
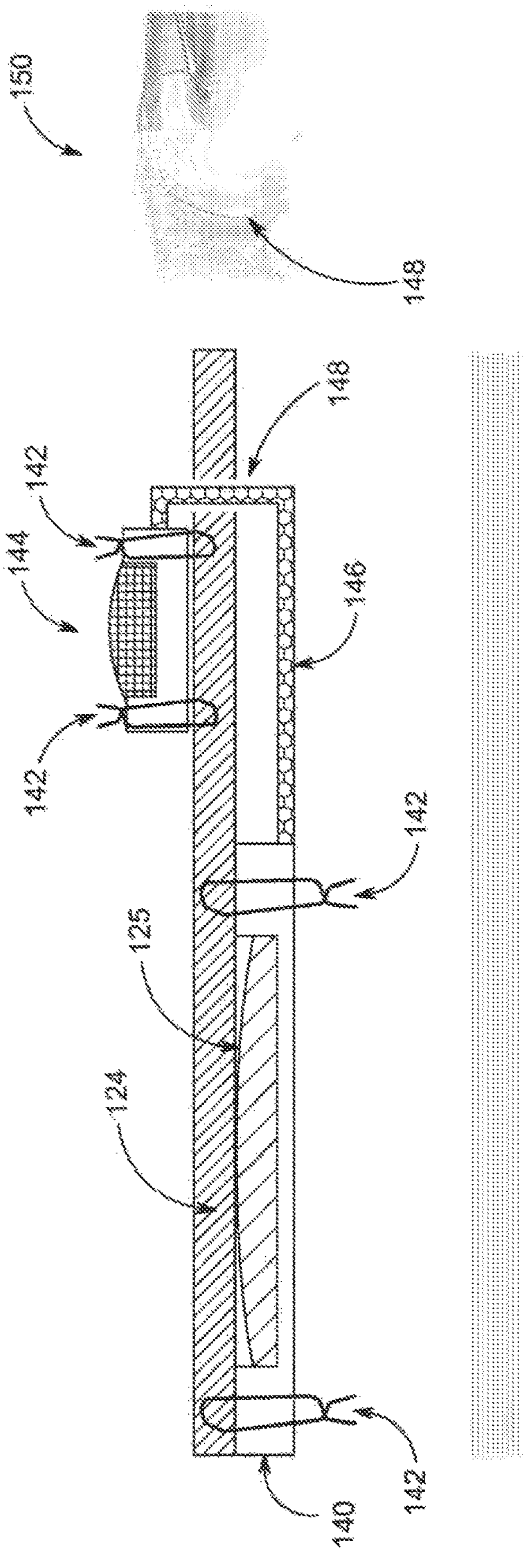
FIG. 8C depicts a side view of a schematic diagram portraying a novel tissue expander device in a pre-expansion state comprising an external port with connection tubing traversing the lower abdominal incision, according to at least some embodiments disclosed herein.
Figure 8D:
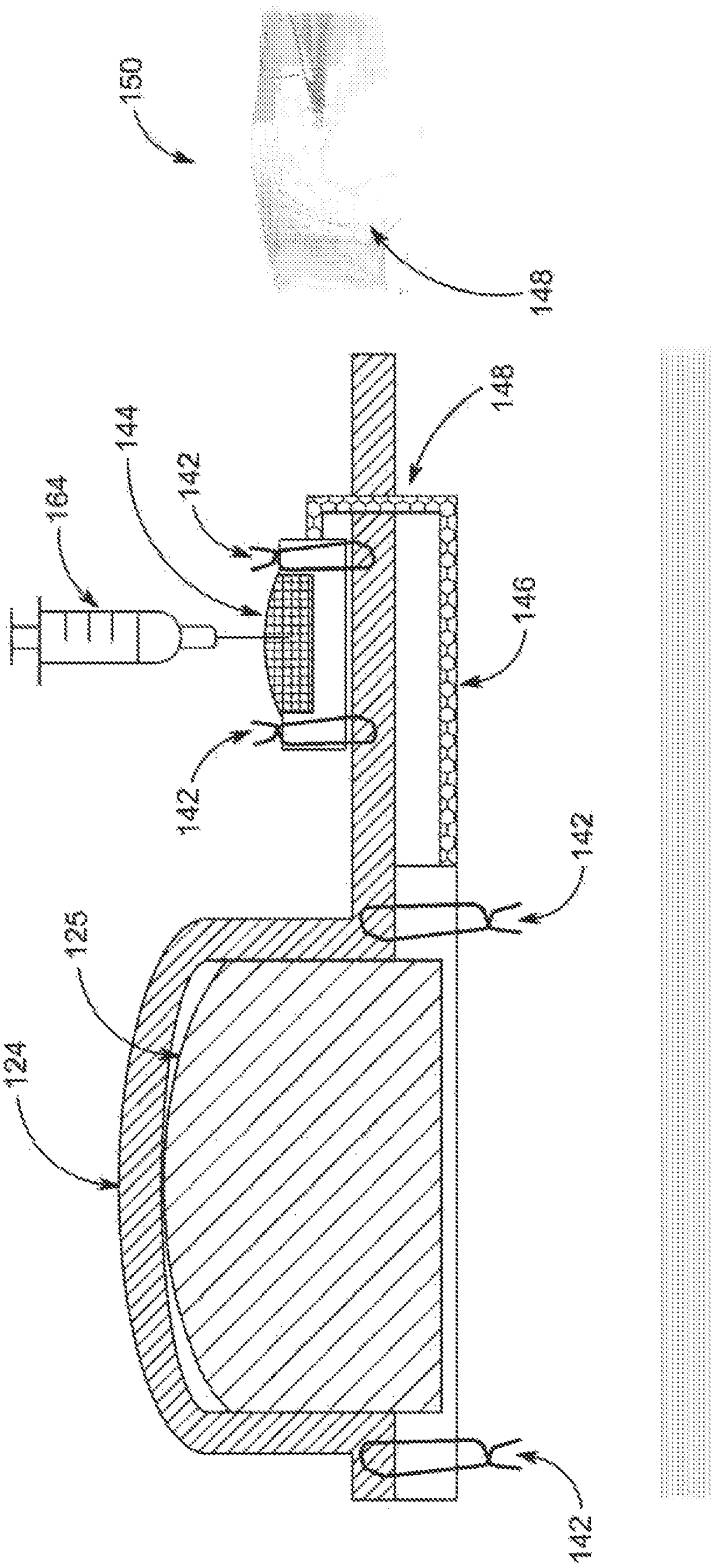
FIG. 8D depicts a side view of a schematic diagram portraying a novel tissue expander device in a post-expansion state comprising an external port after a saline injection into the injection port occurs with connection tubing traversing the lower abdominal incision, according to at least some embodiments disclosed herein.

A third embodiment of the novel tissue expander device 126 comprises an external injection port 144, as shown in FIG. 8A, FIG. 8B, FIG. 8C, and FIG. 8D. Specifically, FIG. 8A depicts an overhead view of a schematic diagram portraying the novel tissue expander device 126 with a round-shaped base comprising the external injection port 144 in a pre-expansion state and FIG. 8B depicts an overhead view of a schematic diagram portraying the novel tissue expander device 126 with an oval-shaped base comprising the external injection port 144 in a pre-expansion state. Further, FIG. 8C depicts a side view of a schematic diagram portraying the novel tissue expander device 126 comprising the external injection port 144 in a pre-expansion state with connection tubing 146 traversing the lower abdominal incision and FIG. 8D depicts a side view of a schematic diagram portraying the novel tissue expander device 126 comprising the external injection port 144 in a post-expansion state after saline injection occurs into the external injection port 144 with the connection tubing 146 traversing the lower abdominal incision.

The novel tissue expander device 126 of the third embodiment includes the rigid body casing comprised of the rigid base/base plate 140 (of FIG. 8C and FIG. 8D), a cylindrical sidewall, and an anchoring ledge at the top where the novel tissue expander device 126 is affixed to the undersurface of the abdominal skin 124 using sutures 142. In general, and as shown in FIG. 8A and FIG. 8B, the rigid base/base plate 140 has the first end 186 disposed opposite the second end 188. The first end 186 may be round in shape (as shown in FIG. 8A) or oval in shape (as shown in FIG. 8B). Moreover, FIG. 8A and FIG. 8B depict the apertures 134 disposed on a circumference of the rigid base/base plate 140. The individual apertures 134 may each receive deep dermal stitches 142 with interposing plastic to be tied over.

Contained within this rigid body casing is the expandable balloon 125 that is connected to the external injection port 144 (e.g., located external to the abdominal skin 124) with connection tubing 146. In this embodiment, injection of the external injection port 144 with saline causes the expandable balloon 125 filling. As a result of this closed-bottom design, expansion of the expandable balloon 125 exerts only upward forces against the abdominal skin 124 with all posterior forces resisted by counterforces provided by the rigid body casing and its skin attachments, thereby optimizing safety.

In this embodiment, and as shown in FIG. 8D, the saline injection 164 fills the expander balloon 125 and expansion occurs directly against the undersurface of the abdominal skin 124. Once the tissue expansion has attained a skin tube of desired height (about equal to the thickness of the abdominal flap), the novel tissue expander device 126 is removed in a second procedure and the skin tube inverted and secured down to the abdominal wall fascia as a scarless neo-umbilicus.

Fourth Embodiment

Figure 9A:
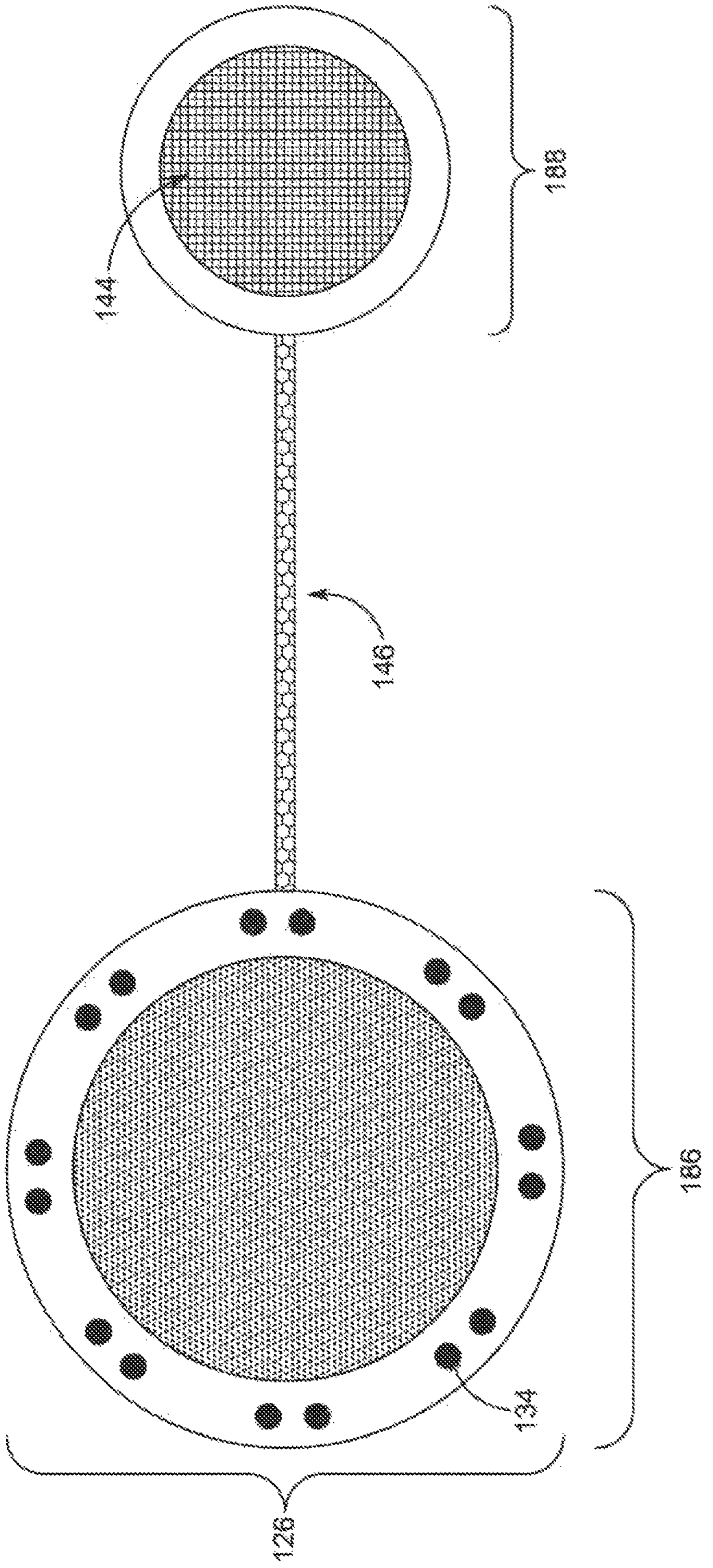
FIG. 9A depicts an overhead view of a schematic diagram portraying a novel tissue expander device with a round-shaped base comprising an external port and a rigid closed-base thimble component in a pre-expansion state, according to at least some embodiments disclosed herein.
Figure 9B:
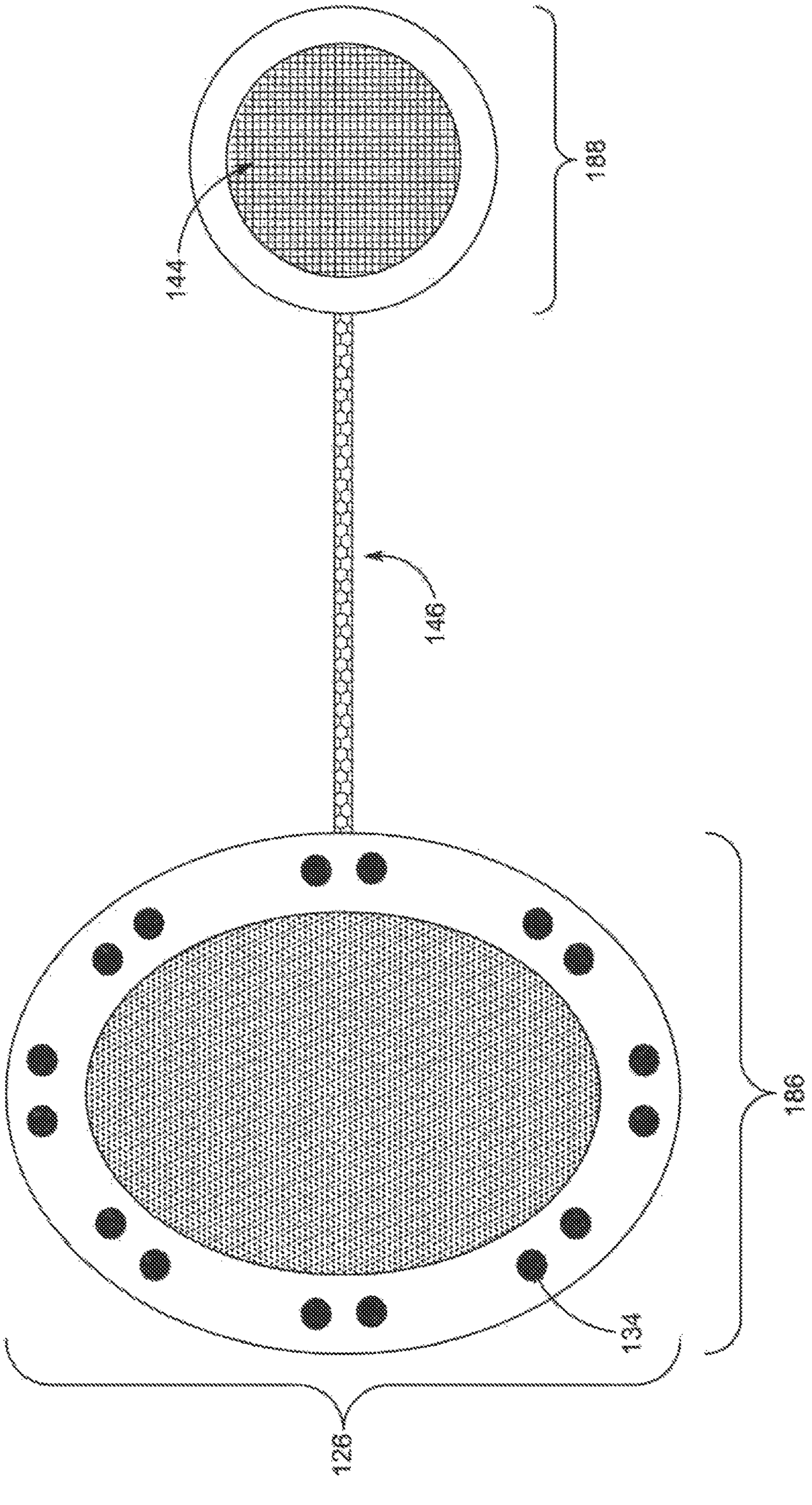
FIG. 9B depicts an overhead view of a schematic diagram portraying a novel tissue expander device with an oval-shaped base comprising an external port and a rigid closed-base thimble component in a pre-expansion state, according to at least some embodiments disclosed herein.
Figure 9C:
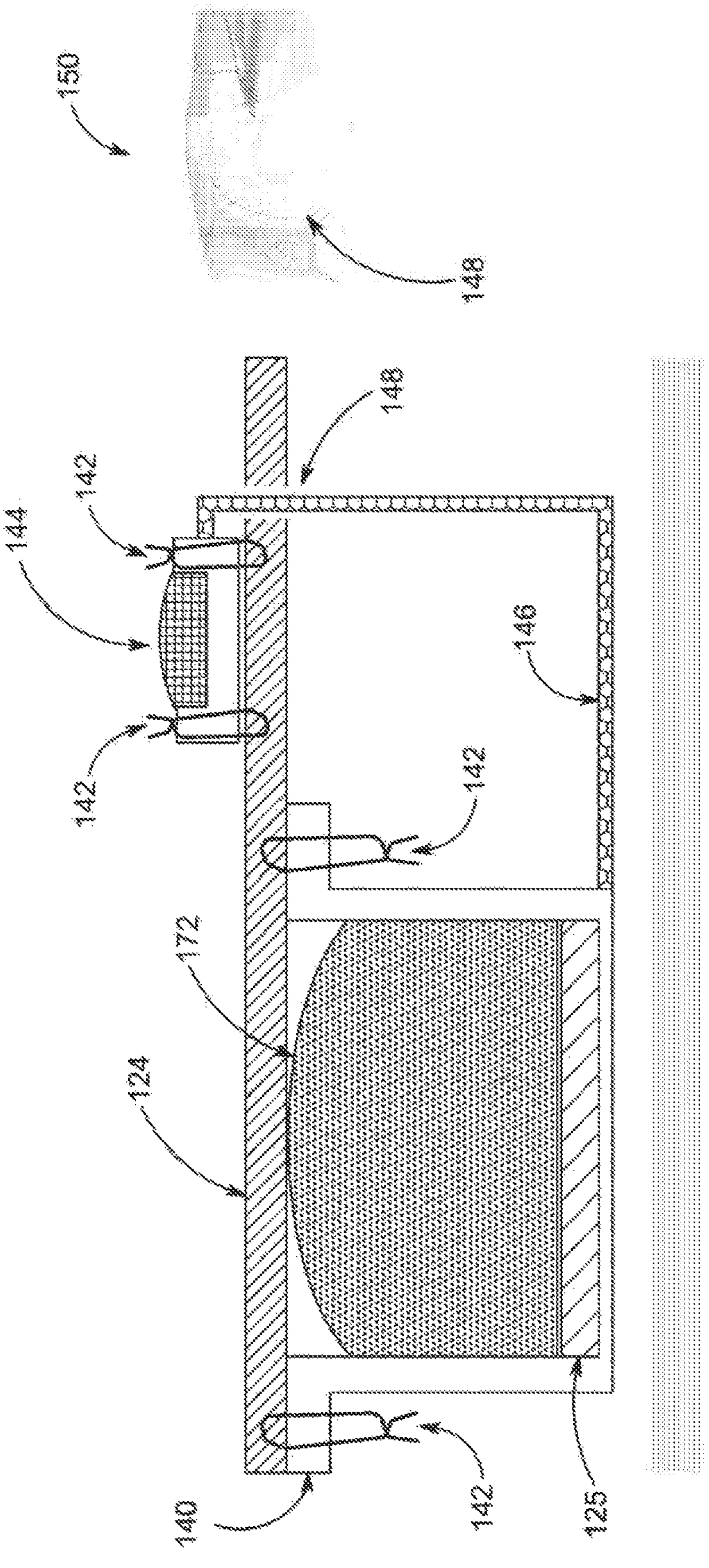
FIG. 9C depicts a side view of a schematic diagram portraying a novel tissue expander device in a pre-expansion state, comprising an external port and a rigid closed-base thimble component with connection tubing traversing the lower abdominal incision, according to at least some embodiments disclosed herein.
Figure 9D:
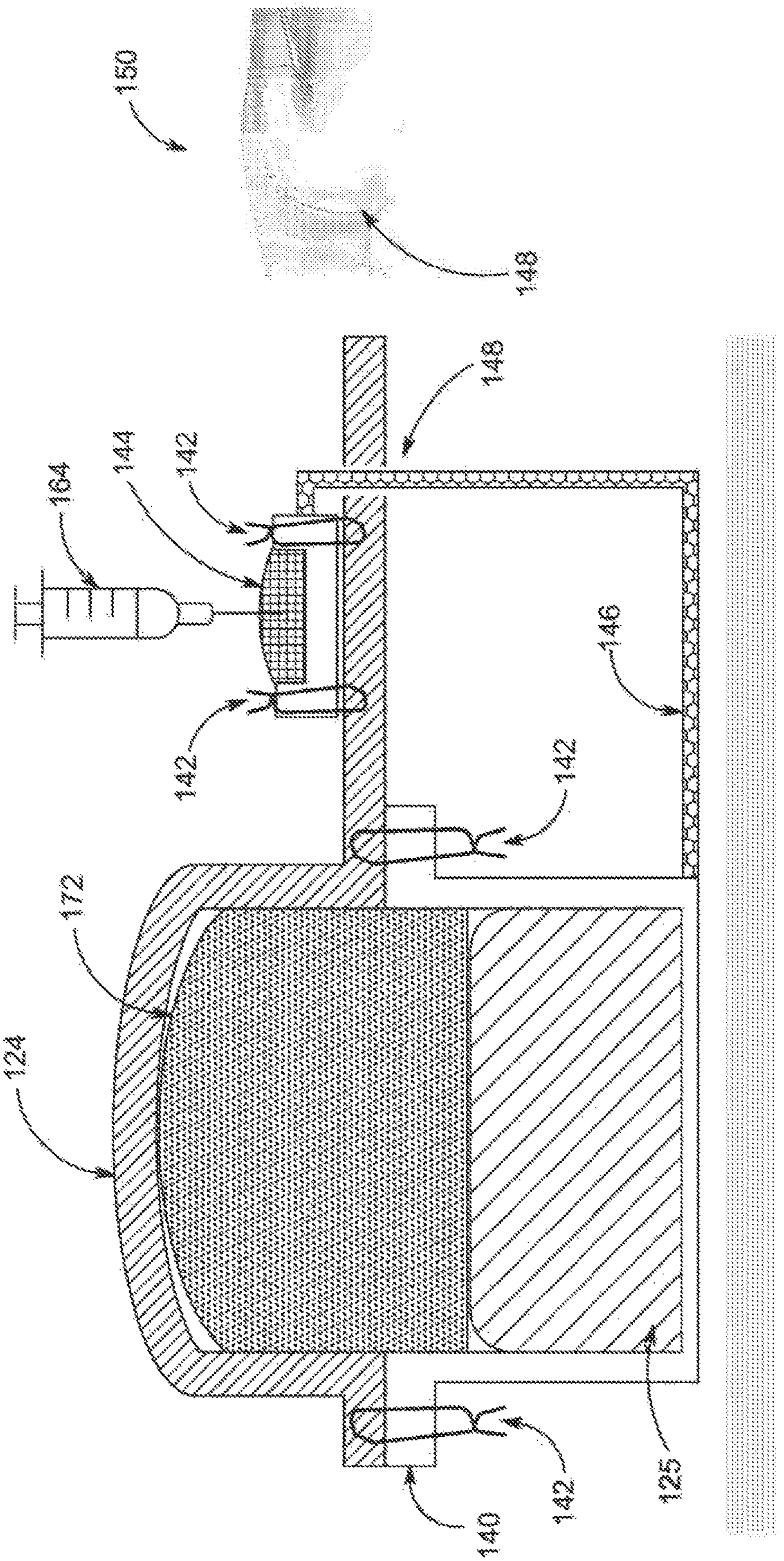
FIG. 9D depicts a side view of a schematic diagram portraying a novel tissue expander device in a post-expansion state, comprising an external port and a rigid closed-base thimble component after a saline injection into the injection port occurs with connection tubing traversing the lower abdominal incision, according to at least some embodiments disclosed herein.

A fourth embodiment of the novel tissue expander device 126 comprises the external injection port 144 and the rigid closed-base thimble component 172, as shown in FIG. 9A, FIG. 9B, FIG. 9C, and FIG. 9D. Specifically, FIG. 9A depicts an overhead view of a schematic diagram portraying the novel tissue expander device 126 with a round-shaped base comprising the external injection port 144 and the rigid closed-base thimble component 172 in a pre-expansion state and FIG. 9B depicts an overhead view of a schematic diagram portraying the novel tissue expander device 126 with an oval base comprising the external injection port 144 and the rigid closed-base thimble component 172 in a pre-expansion state. Further, FIG. 9C depicts a side view of a schematic diagram portraying the novel tissue expander device 126 comprising the external injection port 144 and the rigid closed-base thimble component 172 in a pre-expansion state with connection tubing 146 traversing the lower abdominal incision and FIG. 9D depicts a side view of a schematic diagram portraying the novel tissue expander device 126 comprising the external injection port 144 and the rigid closed-base thimble component 172 in a post-expansion state after saline injection into the external injection port 144 with the connection tubing 146 traversing the lower abdominal incision.

The configuration of the fourth embodiment of the novel tissue expander device 126 is substantially similar to the configuration of the third embodiment of the novel tissue expander device 126, with the exception that the fourth embodiment of the novel tissue expander device 126 additionally includes the rigid closed-base thimble component 172. As shown in FIG. 9D, the saline injection 164 fills the internal injection port 138 and expansion of the expandable balloon 125 occurs against an undersurface of the rigid closed-base thimble component 172, which, in turn, expands against the undersurface of the abdominal skin 124 of the patient 150. Once the tissue expansion has attained a skin tube of desired height (about equal to the thickness of the abdominal flap), the novel tissue expander device 126 is removed in a second procedure and the skin tube is inverted and secured down to the abdominal wall fascia as a scarless neo-umbilicus.

Figure 10:
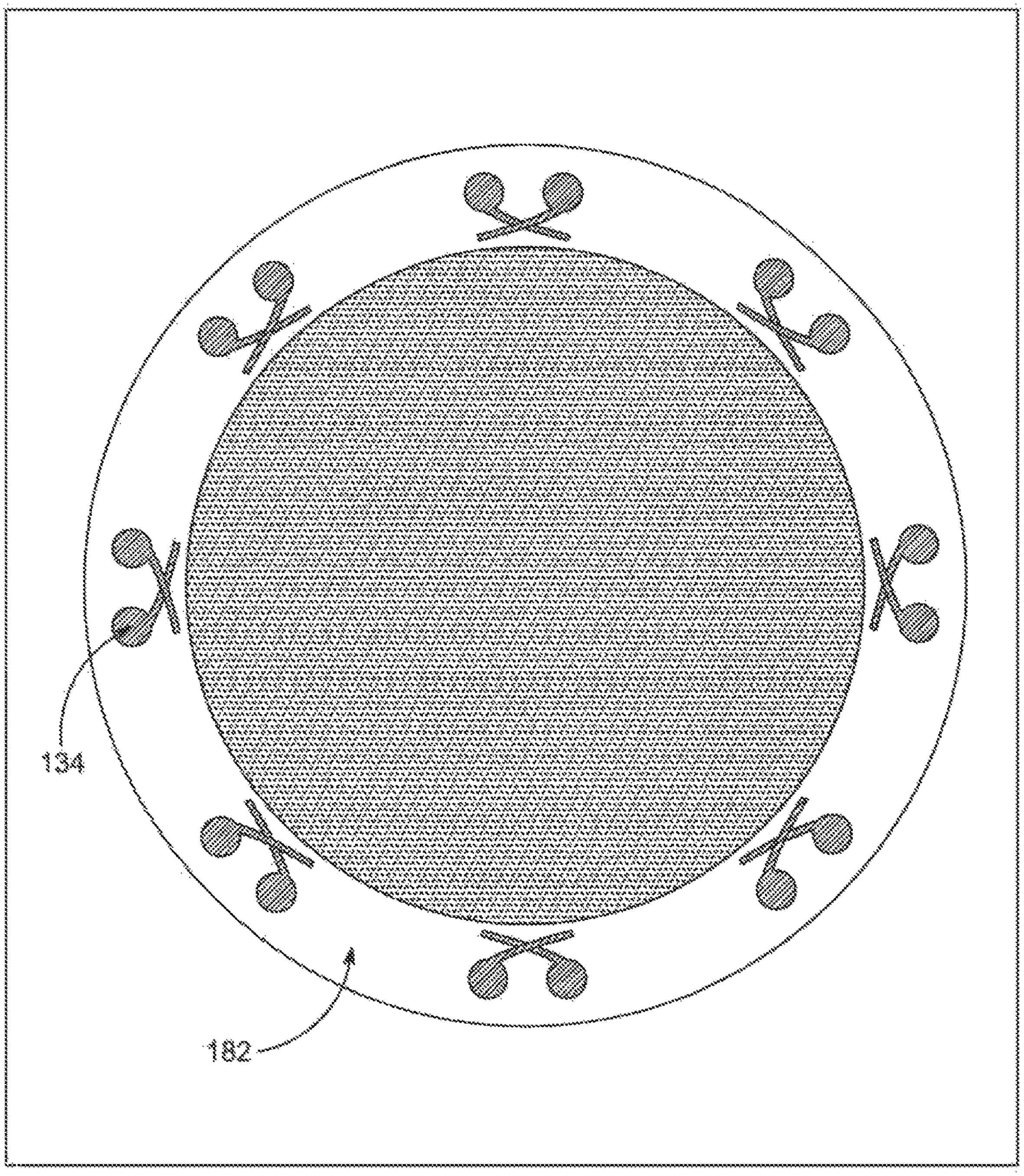
FIG. 10 depicts a schematic diagram of the novel tissue expander device displaying the paired suture apertures within a continuous anchoring ledge, according to at least some embodiments disclosed herein.
Figure 11:
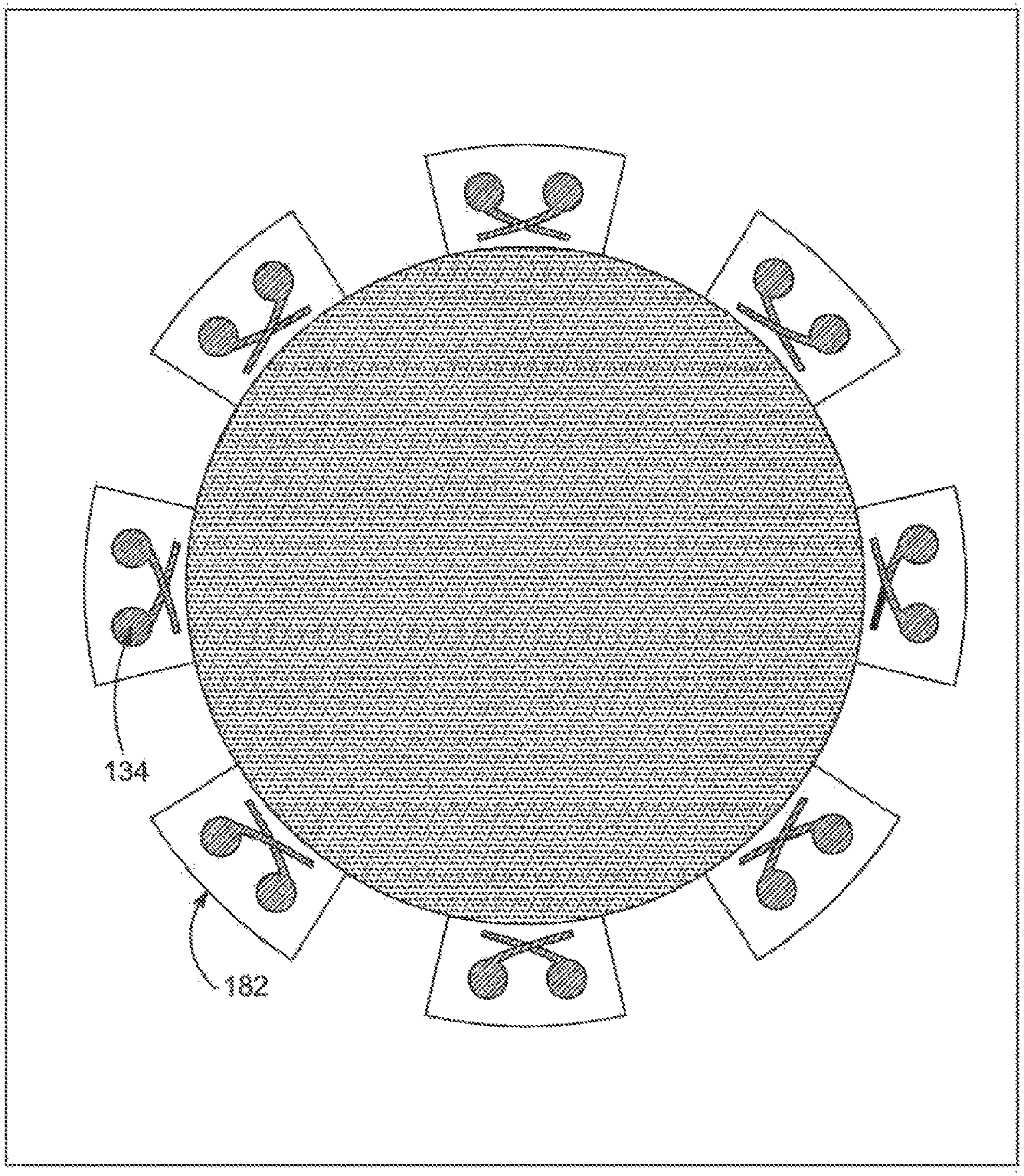
FIG. 11 depicts a schematic diagram of the novel tissue expander device displaying the paired suture apertures within a discontinuous anchoring ledge, according to at least some embodiments disclosed herein.

FIG. 10 depicts a schematic diagram of the novel tissue expander device 126 displaying paired suture apertures 134 within a continuous anchoring ledge 182 and FIG. 11 depicts a schematic diagram of the novel tissue expander device 126 displaying the paired suture apertures 134 within a discontinuous anchoring ledge 182.

Figure 12:
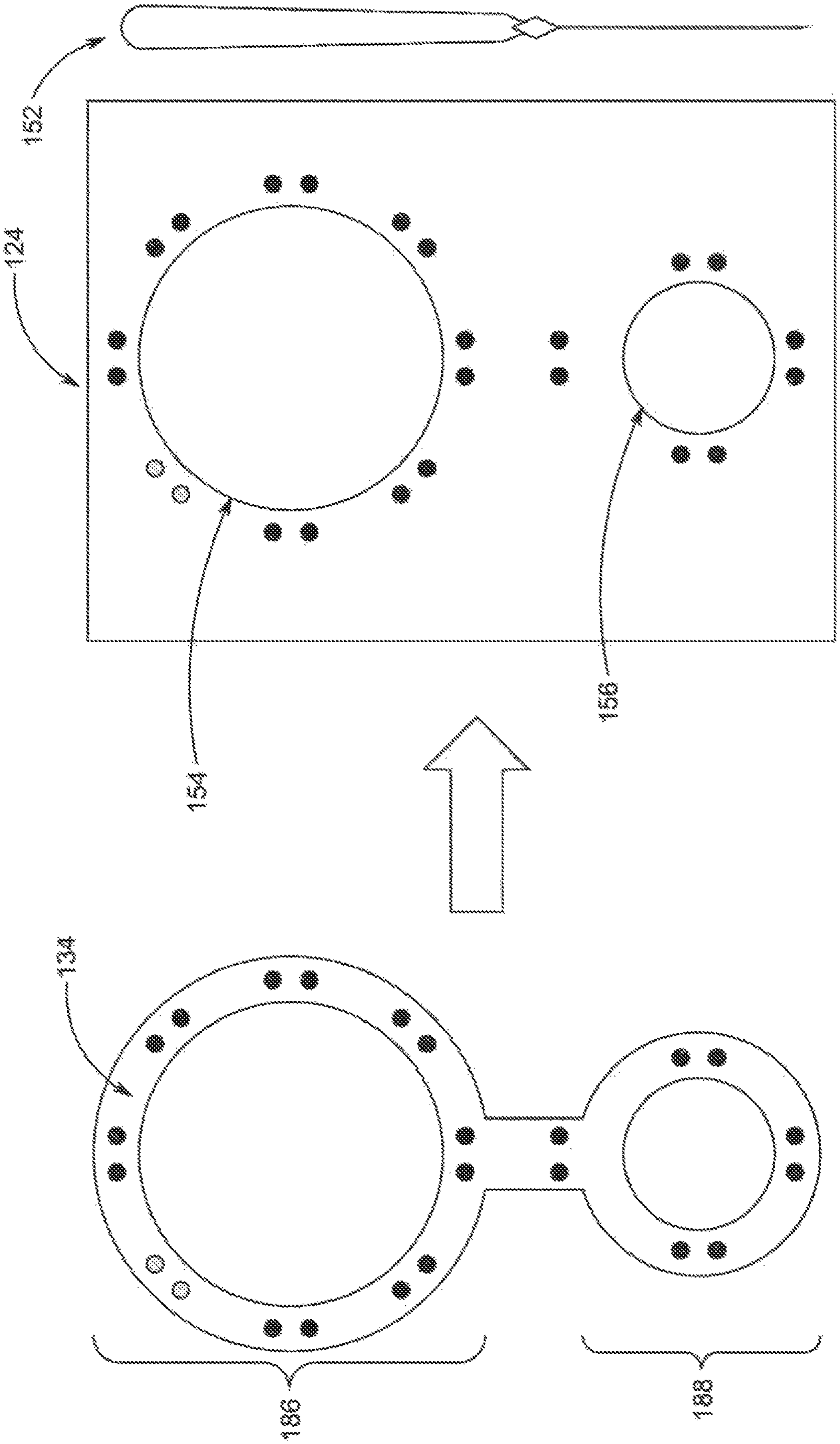
FIG. 12 depicts an overhead view of a schematic diagram portraying a stencil for the novel tissue expander device comprising an internal port being positioned and suture points marked, according to at least some embodiments disclosed herein.
Figure 13:
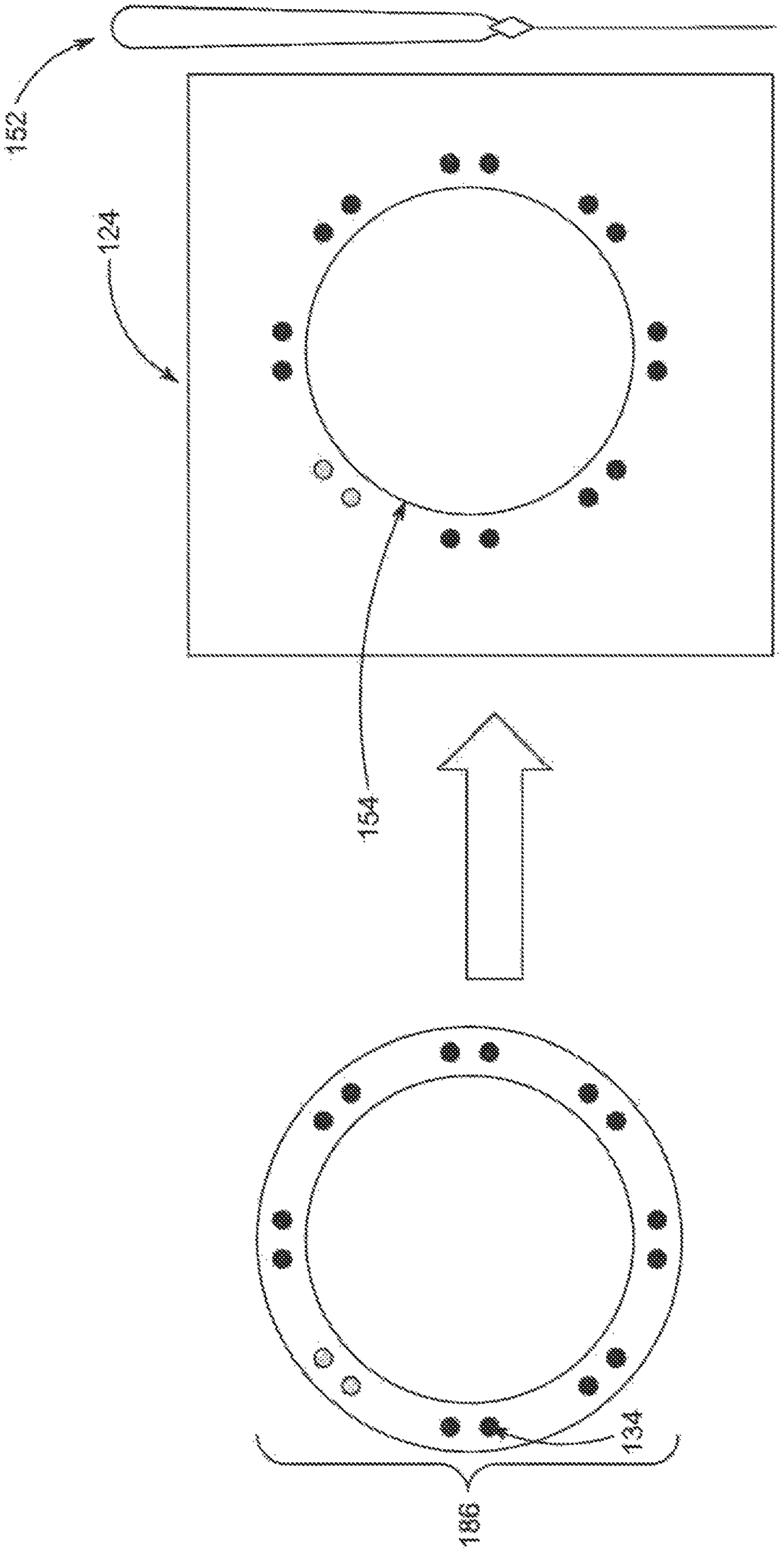
FIG. 13 depicts an overhead view of a schematic diagram portraying a stencil for the novel tissue expander device comprising an external port being positioned and suture points marked, according to at least some embodiments disclosed herein.

FIG. 12 depicts an overhead view of a schematic diagram portraying a stencil for the novel tissue expander device 126 comprising the internal injection port 138 being positioned and suture points marked and FIG. 13 depicts an overhead view of a schematic diagram portraying a stencil for the novel tissue expander device 126 comprising the external injection port 144 being positioned and suture points marked. The central and suture apertures 154, 156 are marked with ink and are shown in FIG. 12 and FIG. 13. A Reverdin needle 152 that is used to pass through the abdominal skin 124 prior to insertion of the novel tissue expander device 126 is also depicted in FIG. 12 and FIG. 13.

Figure 14A:
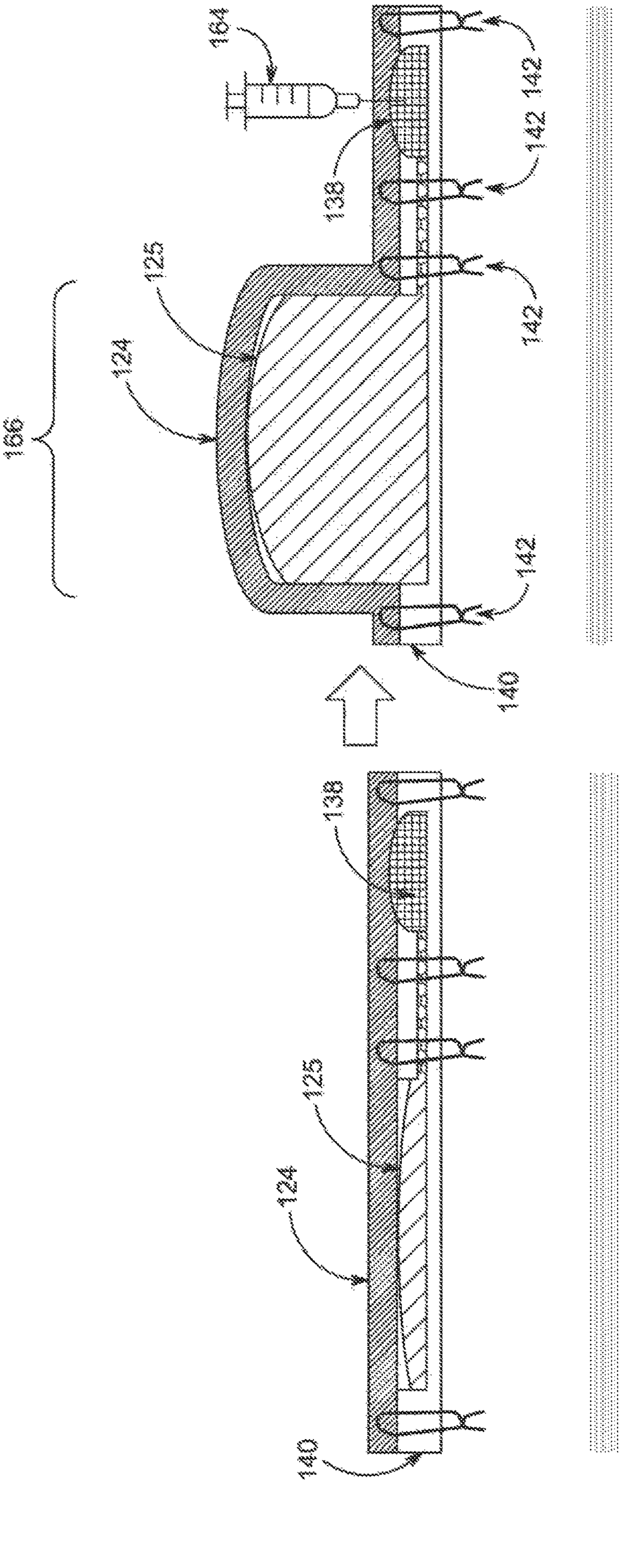
FIG. 14A depicts schematic diagrams of process steps executed using the novel tissue expander device comprising an internal port in pre- and post-expansion state, including: anchoring to the to the undersurface of the abdominal skin, filling an expander balloon with saline injections, and expanding and growing a skin tube, according to at least some embodiments disclosed herein.
Figure 14B:
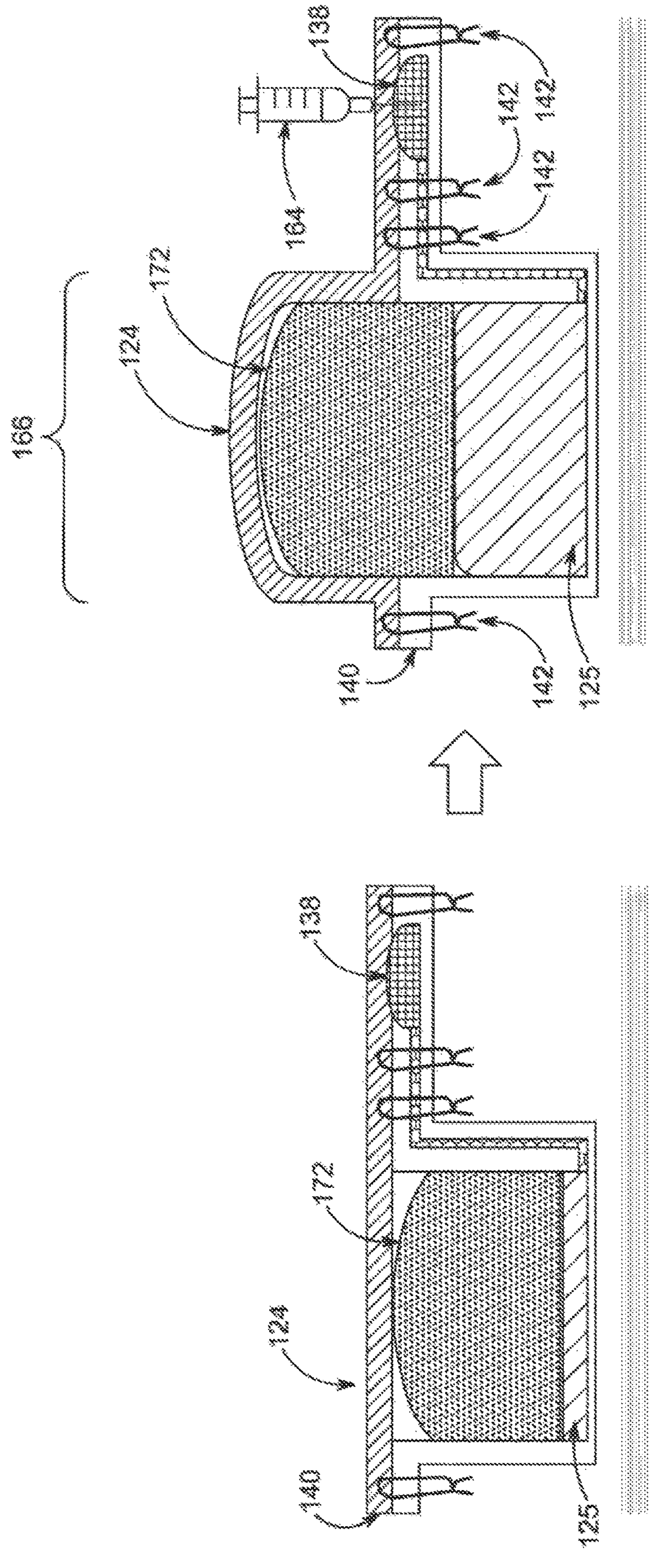
FIG. 14B depicts schematic diagrams of process steps executed using the novel tissue expander device comprising an internal port and a rigid closed-base thimble component in pre- and post-expansion state, including: anchoring to the to the undersurface of the abdominal skin, filling an expander balloon with saline injections, and expanding and growing a skin tube, according to at least some embodiments disclosed herein.
Figure 14C:
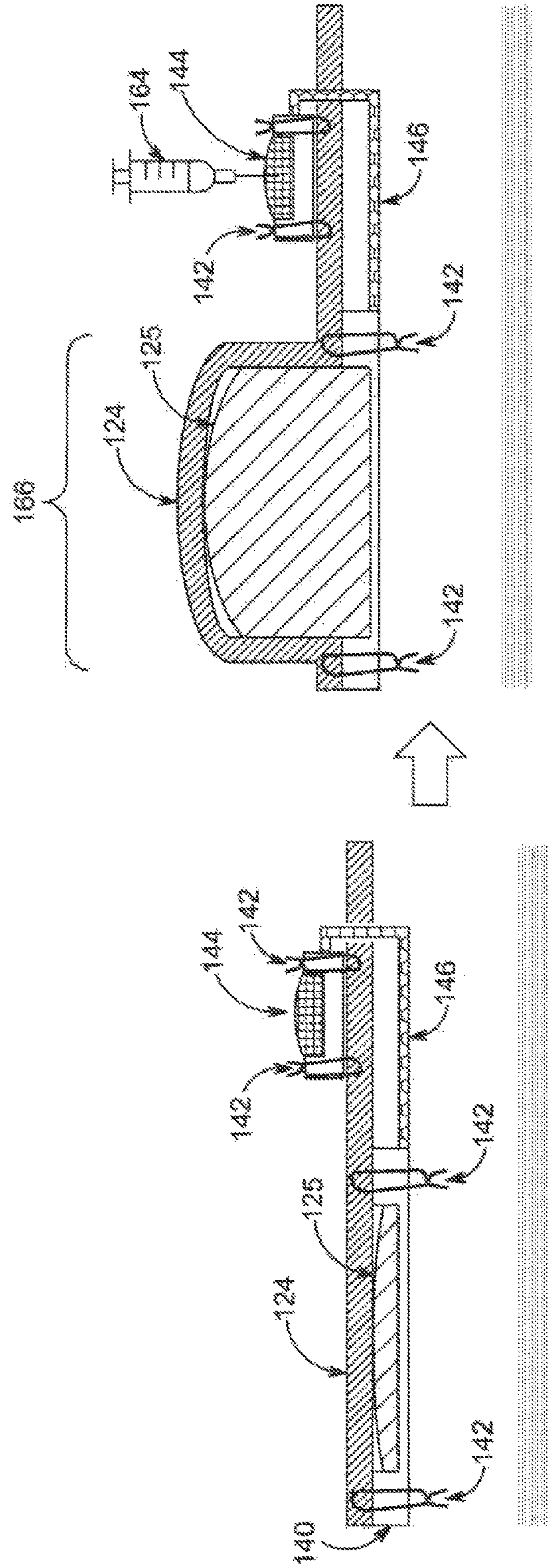
FIG. 14C depicts schematic diagrams of process steps executed using the novel tissue expander device comprising an external port in pre- and post-expansion state, including: anchoring to the to the undersurface of the abdominal skin, filling an expander balloon with saline injections, and expanding and growing a skin tube, according to at least some embodiments disclosed herein.
Figure 14D:
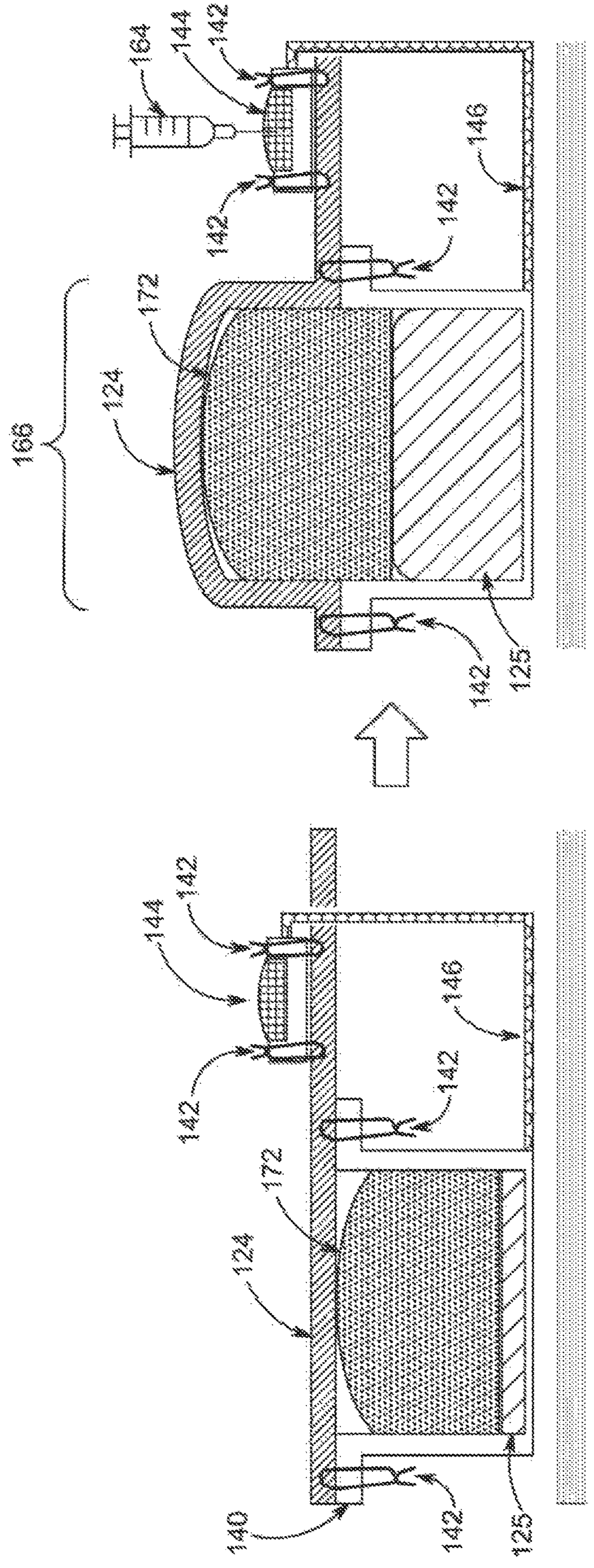
FIG. 14D depicts schematic diagrams of process steps executed using the novel tissue expander device comprising an external port and a rigid closed-base thimble component in pre- and post-expansion state, including: anchoring to the to the undersurface of the abdominal skin, filling an expander balloon with saline injections, and expanding and growing a skin tube, according to at least some embodiments disclosed herein.
Figure 14E:
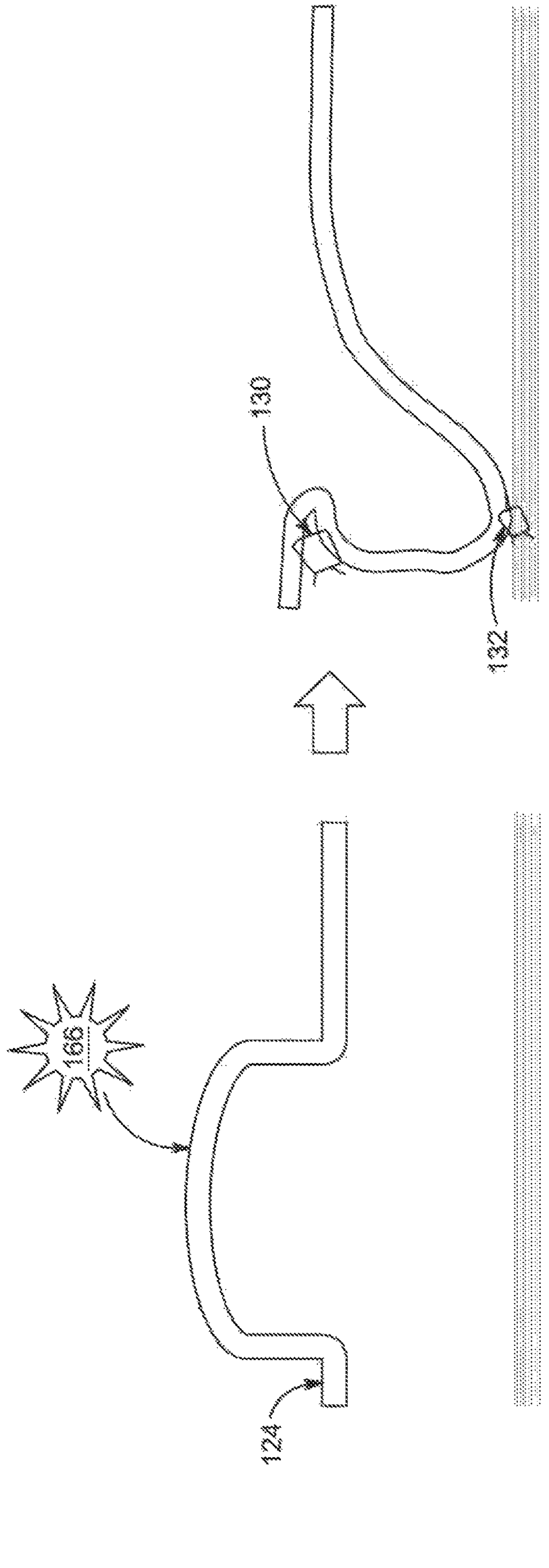
FIG. 14E depicts schematic diagrams of process steps to remove the novel tissue expander device during a second procedure subsequent the process steps of FIG. 14A, FIG. 14B, FIG. 14C, or FIG. 14D to allow for skin tube inversion and attachment to the abdominal wall fascia to complete the neo-umbilicoplasty, according to at least some embodiments disclosed herein.

FIG. 14A depicts schematic diagrams of process steps executed using the novel tissue expander device 126 comprising an internal injection port 138 in pre- and post-expansion state and FIG. 14C depicts schematic diagrams of process steps executed using the novel tissue expander device 126 comprising the external injection port 144 in pre- and post-expansion state. FIG. 14B depicts schematic diagrams of process steps executed using the novel tissue expander device 126 comprising the internal injection port 138 and the rigid closed-base thimble component 172 in pre- and post-expansion state and FIG. 14D depicts schematic diagrams of process steps executed using the novel tissue expander device 126 comprising the external port 144 and the rigid closed-base thimble component 172 in pre- and post-expansion state. FIG. 14E depicts schematic diagrams of process steps to remove the novel tissue expander device 126 during a second procedure subsequent the process steps of FIG. 14A, FIG. 14B, FIG. 14C, or FIG. 14D to allow for skin tube inversion and attachment to the abdominal wall fascia to complete the neo-umbilicoplasty.

For FIG. 14A, FIG. 14B, FIG. 14C, and FIG. 14D in the pre-expansion state, the novel tissue expander device 126 is located beneath the abdominal skin 124. For the embodiments of FIG. 14A and FIG. 14B, a magnet is used to locate the internal injection port 138 located under the abdominal skin 124. Next, the saline injection 164 is received by the internal injection port 138 (in FIG. 14A and FIG. 14B) or by the external injection port 144 (of FIG. 14C and FIG. 14D).

When the saline injection 164 fills the expander balloon 125 in FIG. 14A and FIG. 14C, expansion occurs directly against the undersurface of the abdominal skin 124. Once the tissue expansion has attained a skin tube of desired height (about equal to the thickness of the abdominal flap), the novel tissue expander device 126 is removed in a second procedure.

Specifically, FIG. 14B and FIG. 14D additionally include the rigid closed-base thimble component 172 such that when the saline injection 164 fills the internal injection port 138 or the external injection port 144, expansion of the expander balloon 125 occurs against an undersurface of the rigid closed-base thimble component 172, which, in turn, expands against the undersurface of the abdominal skin 124 of the patient 150. Once the tissue expansion has attained a skin tube of desired height (about equal to the thickness of the abdominal flap), the novel tissue expander device 126 is removed in a second procedure.

Specifically, creation of an umbilical neo-stalk 166 on the abdominal skin flap is shown in FIG. 14A, FIG. 14B, FIG. 14C, FIG. 14D, and FIG. 14E. The umbilical neo-stalk 166 on the abdominal skin flap may be inverted as an aesthetically pleasing neo-umbilicus. Specifically, as shown in FIG. 14E, a first process step 130 occurs to recreate the superior hooding and a second process step 132 occurs to ensure securement to the abdominal wall fascia. Thus, use of the novel tissue expander device 126 of the present invention results in a natural and aesthetically pleasing umbilicus that has a midline position and is free of scar-related deformities.

Other embodiments and variations of the novel tissue expander device for creating a scarless expansion and deformation of the skin can be used to create protrusions and/or depressions in the skin. For example, embodiments having a smaller base plate and inflatable balloon may be used to create a scarless, natural-appearing nipple. This may be desirable either because one does not exist, due to congenital (e.g. amastia or athelia) or acquired causes (e.g. mastectomy for treatment of breast cancer necessitating removal of the nipple-areolar complex as part of the tissue specimen), or the like. Or, a properly configured and sized expansion device may be used to create or enhance a penile structure, or a nose, or a finger or toe. Openings for introducing and placing such tissue expander devices under the skin may be inconspicuously placed apart from the subject structure, leaving the subject structure itself entirely without a scar. The structure may then be filled with soft material such as a silicone implant, or a firm flexible cartilage-like implant, or a strong inflexible bone-like implant, with or without one or more joints.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

Although the foregoing example embodiments of the invention have been described with a certain degree of particularity, it is to be understood that they have been presented only by way of illustration and that numerous changes in the details of construction and arrangement of parts may be resorted to without departing from the spirit and the scope of the invention.

REFERENCES

The following references, to the extent that they provide exemplary procedural or other details supplementary to those set forth herein, are specifically incorporated herein by reference.

Boudreault, D. J., et al., Getting the Best Results in Abdominoplasty: Current Advanced Concepts, *Plast Reconstr Surg.,* 2019, 143(3), Pages 628e-636e, DOI: 10.1097/PRS.0000000000005378.

da Silva Júnior, V. V. da S., et al., Improvement on the Neo-umbilicoplasty Technique and Review of the Literature, *Aesthet Plast Surg.,* 2017, 41(3), Pages 600-607, DOI: 10.1007/s00266-017-0847-6.

Grazer, F. M., Abdominoplasty, *Plast. Reconstr. Surg.*, June 1973, 51(6), Pages 617-623.

International Society of Aesthetic Plastic Surgery. *International study on aesthetic/cosmetic procedures performed in* 2013. Hanover: International Society of Aesthetic Plastic Surgery; 2014.

International Society of Aesthetic Plastic Surgery. *International study on aesthetic/cosmetic procedures performed in* 2019. Hanover: International Society of Aesthetic Plastic Surgery; 2019.

Joseph, W. J., et al., Creating the Perfect Umbilicus: A Systematic Review of Recent Literature, *Aesthet Plast Surg.,* 2016, 40(3), Pages 372-379, DOI: 10.1007/s00266-016-0633-x.

Kadri, O. M., et al., Abdominoplasty Revision Using Tissue Expansion, *Aesthetic Plast Surg*., June 2013, 37(3), Pages 538-40, DOI: 10.1007/s00266-013-0104-6.

Kelly, H. A. Excision of the fat of the abdominal wall lipectomy, *Surg Gynecol Obstet.,* 1910, 10, Pages 229-31.

Lee, S. J., et al., Computer-Aided Analysis of the 'Beautiful' Umbilicus, *Aesthet Surg J.,* 2014, 34(5), Pages 748-756, DOI: 10.1177/1090820X14533565.

Malic, C. C., et al., Patient Satisfaction with Two Different Methods of Umbilicoplasty, *Plast Reconstr Surg.,* 2007, 119(1), Pages 357-361, DOI: 10.1097/01.prs.0000244907.06440.f8.

Matarasso, A., et al., Abdominoplasty and abdominal contour surgery: a national plastic surgery survey, *Plast Reconstr Surg.,* 2006, 117, Pages 1797-808.

Mejia, J. D., Colombian Clover Umbilicoplasty: Achieving a Natural Looking Belly Button, *Aesthet. Surg. J.,* 2019, 40(3), Pages 342-347, DOI: 10.1093/asj/sjz311.

Pitanguy, I., Abdominal lipectomy: an approach to it through an analysis of 300 consecutive cases, *Plast Reconstr Surg.,* 1967, 40, Pages 384-91.

Reho, A., et al., 'Scarless reverse umbilicoplasty': A new technique of umbilical transposition in abdominoplasty, *J Plastic Reconstr Aesthetic Surg.,* 2019, 72(4), Pages 656-661, DOI: 10.1016/j.bjps.2019.01.024.

Rohrich, R. J., et al., Is the Umbilicus Truly Midline? Clinical and Medicolegal Implications, *Plast. Reconstr. Surg.,* 2003, 112(1), Pages 259-263, DOI: 10.1097/01.PRS.0000066367.41067.C2.

Rozen, S. M., et al., The two-dermal-flap umbilical transposition: a natural and aesthetic umbilicus after abdominoplasty, *Plast. Reconstr. Surg.,* 2007, 119(7), Pages 2255-2262, DOI: 10.1097/01.prs.0000261037.69256.3e.

The Aesthetic Society. Aesthetic Plastic Surgery National Databank Statistics, 2019.

Vernon, S., Umbilical transplantation upward and abdominal contouring in lipectomy, *Am J Surg.,* 1957, 94, Pages 490-492.

Vidal, P., et al., Managing Complications in Abdominoplasty: A Literature Review, *Arch. Plast. Surg.,* 2017, 44(5), Pages 457-468, DOI: 10.5999/aps.2017.44.5.457.

Villegas, F., TULUA Lipoabdominoplasty: No Supraumbilical Elevation Combined With Transverse Infraumbilical Plication, Video Description and Experience With 164 Patients, *Aesthet Surg J.,* 2021, 41(5), Pages 577-594, DOI: 10.1093/asj/sjaa183.

Visconti, G., et al., Concepts in Navel Aesthetic: A Comprehensive Surface Anatomy Analysis, *Aesthet Plast Surg.,* 2015, 39(1), Pages 43-50, DOI: 10.1007/s00266-014-0434-z.

What is claimed is:

1. A device for creating a scarless neo-umbilicus, the device comprising:

a base plate comprising a first end disposed opposite a second end, wherein:

the first end receives an expandable balloon and a rigid closed-base thimble component;

the second end receives an injection port; and the expandable balloon is coupled to the injection port via tubing, and when coupled the expandable balloon is in fluid communication with the injection port;

a rigid body casing having;

a cylindrical sidewall; and an anchoring ledge;

device is affixed to an undersurface of the abdominal skin using sutures;

in response to the expandable balloon receiving saline injection from the injection port, the expandable balloon, constrained by the cylindrical sidewall, expands against the bottom of the rigid closed-base thimble component and pushes the rigid closed-base thimble component against an undersurface of the abdominal skin;

device is removed when the abdominal skin attains a skin tube of a desired height; and the skin tube is inverted and secured to the underside of the abdominal wall fascia as a scarless neo-umbilicus.

2. The device of claim 1, wherein the cylindrical sidewall is one of a circular, oval, or elliptic right cylinder.

3. The device of claim 1, wherein the anchoring ledge includes a plurality of spaced apart paired apertures for receiving sutures to suture the device to an undersurface of the abdominal skin.

4. The device of claim 1, wherein the injection port initially has a circular shape less than 3 cm in diameter.

5. The device of claim 1, wherein an inner diameter of the tubing is less than 4 mm.

6. The device of claim 1, wherein expansion of the expandable balloon causes the expandable balloon, constrained by the rigid body casing, to press against a proximal end of the rigid closed-base thimble component, which causes a distal end of the rigid closed-base thimble component to press against an undersurface of the abdominal skin.

7. The device of claim 1, wherein the base plate comprises a shape selected from the group consisting of: a round shape, an oval shape, and an elliptical shape.

8. The device of claim 1, wherein the injection port is an internal injection port located beneath abdominal skin of a patient.

9. The device of claim 1, wherein the expandable balloon, the connection tubing, and the internal injection port comprise a silicone elastomer material or an expandable biocompatible material.

10. The device of claim 9, wherein the rigid body casing and the rigid closed-base thimble component comprise a rigid biocompatible plastic material.

* * * * *